US006200799B1

(12) United States Patent
Shaw et al.

(10) Patent No.: US 6,200,799 B1
(45) Date of Patent: Mar. 13, 2001

(54) SOMATIC GENE THERAPY TO SUPPRESS SECONDARY CATARACT FORMATION FOLLOWING EYE SURGERY

(75) Inventors: Phillip Herbert Shaw; Roland Sahli; Michel Sickenberg, all of Lausanne; Francis Munier, Gandvaux, all of (CH)

(73) Assignee: University of Lausanne, Lausanne (CH)

( * ) Notice: Subject to any disclaimer, the term of this patent is extended or adjusted under 35 U.S.C. 154(b) by 0 days.

(21) Appl. No.: 08/867,902

(22) Filed: Jun. 3, 1997

(51) Int. Cl.[7] .......................... C12N 15/86; C12N 15/861
(52) U.S. Cl. ...................... 435/320.1; 435/455; 435/456; 424/93.2
(58) Field of Search ..................... 424/93.2; 435/320.1, 435/455, 456; 514/44

(56) References Cited

PUBLICATIONS

Orkin et al., "Report and recommendations of the panel to assess the NIH investment in research on gene therapy", issued by the U.S. National Institutes of Health, Dec. 1995.*
Verma et al., "Gene therapy–promises, problems and prospects", Nature 389: 239–242, Sep. 1997.*
Murata et al., "Ocular gene therapy: Experimental studies and clinical possibilities", Ophthalmic Res. 29: 242–251, Sep. 1997.*
Borrás et al., "Ocular adenovirus gene transfer varies in efficiency and inflammatory response", Invest. Ophthalmol. Vis. Sci. 37: 1282–1293, Jun. 1996.*

* cited by examiner

Primary Examiner—Scott D. Priebe
(74) Attorney, Agent, or Firm—Ivor R. Elrifi; Kristin E. Konzak; Mintz, Levin, Cohn, Ferris, Glovsky & Popeo

(57) ABSTRACT

A replication-defective recombinant virus, preferably an adenovirus that lacks E1a, E1b and E4 ORF 6, capable of infecting an eye and containing a ORF encoding a protein that when expressed in lens epithelial cells of an eye, suppresses, at the level of the germinative epithelium of the lens of the eye, cellular proliferation which is stimulated by eye surgery and which would otherwise result in secondary cataract formation in the eye is disclosed. The ORF, to be expressed, is under the control of a promoter sequence which is expressly exclusively in human lens epithelial cells. The preferred ORFs, to be expressed, include a non-phosphorylatable retinoblastoma ORF, a dominant negative mutant of a human RAS ORF and a Herpes thymidine kinase ORF. The preferred promoter sequences include: a) a promoter of a human Major Intrinsic Protein gene, particularly from −259 nt to +34 nt, b) a promoter of a human β crystallin gene, particularly from −345 nt to +45 nt, and especially c) the promoter of the Major Intrinsic Protein gene or β crystallin gene or portions thereof, in combination with elements of the promoter of the rat Early Growth Response-1 gene, from −518 nt to −236 nt. Use of the recombinant virus for the treatment of an eye, undergoing eye (e.g. cataract) surgery, in order to reduce the incidence of cellular proliferation in the eye following the surgery, and thereby to prevent the formation of secondary cataracts is disclosed.

5 Claims, 30 Drawing Sheets

Rat EGR-1 promoter sequence

-538

GATCTAGCCTCAGCTCTACGCGCCTGGCGCCCTCCCTACGCGGGCGTCCC

CGACTCCCGCGCGCGTTCAGGCTCCGGGTTGGGAACCAAGGAGGGGGAGG

GTGGGTGCGCCGACCCGGAAACACCATATAAGGAGCAGGAAGGATCCCCC

GCCGGAACAGACCTTATTTGGGCAGCGCCTTATATGGAGTGGCCCAATAT

GGCCCTGCCGCTTCCGGCTCTGGGAGGAGGGGCGAACGGGGTTGGGGCG

GGGGCAAGCTGGGAACTCCAGGAGCCTAGCCCGGGAGGCCACTGCCGCTG

TTCCAATACTAGGCTTTCCAGGAGCCTGAGCGCTCAGGGTGCCGGAGCCG

GTCGCAGGGTGGAAGCGCCCACCGCTCTTGGATGGGAGGTCTTCACGTCA

CTCCGGGTCCTCCCGGTCGGTCCTTCCATATTAGGGCTTCCTGCTTCCCA

TATATGGCCATGTACGTCACGGCGGAGGCGGGCCCGTGCTGTTTCAGACC

CTTGAAATAGAGGCCGATTCGGGGAGTCGCGAGAGATCCAGCGCGCAGA

ACTTGGGGAGCCGCCGCCGCGATTCGCCGCCGCCGCCAGCTTCCGCCGCC

GCAAGATCGGCCCCTGCCCCAGCCTCCGCGGCAGCCCTGCGTCCACCACG

GGCCGCGGCCACCGCCAGCCTGGGGCCCACCTACACTCCCCGCAGTGTG

AGCT

Dom. Neg. ras (1155 bps)

Mip promoter sequence

-259

GATCTTTCCAGTCCTGCTGTTCTTCACCCCCACTTCTCGTAGTCTCTCTT

GCTGTGACCCCAATCCCACCCTCACTGCCATGGCTCTCTCGGCTCATCTC

CCAGTTGAGAAAGGCGGGAAAATCCAGCATTTTTACCATGTAGGGGAGGG

GACTTAGCCCTCCACAGCTGTGAAGGGGTTAAGAGGCTGGGCCTGCTACC

TCAGCCTGCCCCTCCCAGGGATTAGGAGTCCTCTATAAAGGGGACTGTCC

ACCCAGACAAGGCCATGGGGGTAGCAGGGACCCAGGCACTGTGACCATGA

GCT

Composite 1 promoter sequence:

-538 of EGR-1

GATCTAGCCTCAGCTCTACGCGCCTGGCGCCCTCCCTACGCGGGCGTCCC

CGACTCCCGCGCGTTCAGGCTCCGGGTTGGGAACCAAGGAGGGGAGG

GTGGGTGCGCCGACCCGGAAACACCATATAAGGAGCAGGAAGGATCCCCC

GCCGGAACAGACCTTATTTGGGCAGCGCCTTATATGGAGTGGCCCAATAT

GGCCCTGCCGCTTCCGGCTCTGGGAGGAGGGGCGAACGGGGGTTGGGGCG

GGGGCAAGCTGGGAACTCCAGGAGCCTAGCCCGATCTTTCCAGTCCTGCT

GTTCTTCACCCCCACTTCTCGTAGTCTCTCTTGCTGTGACCCCAATCCCA

CCCTCACTGCCATGGCTCTCTCGGCTCATCTCCCAGTTGAGAAAGGCGGG

AAAATCCAGCATTTTTACCATGTAGGGAGGGGACTTAGCCCTCCACAGC

TGTGAAGGGGTTAAGAGGCTGGGCCTGCTACCTCAGCCTGCCCCTCCCAG

GGATTAGGAGTCCTCTATAAGGGGACTGTCCACCCAGACAAGGCCATGG

+156 of MIP

GGGTAGCAGGGACCCAGGCACTGTGACCATGAGCT

Fig. 14A

β Crystallin promoter sequence

-330
GATCTCCCAGGGTCTTAAGGTCTTAGGAAGATCCCAAGGTGGTGTGAGGA

ACNTGGAGAAGGACAAGAGACAAGTACTCATGGCAGAGACTTCTGTCCTC

ACCCCCTAGCTGCTCTGAGAGATTAAGAAAGCCAAGGCCTGCAGCAGCCA

GCCATGCCCACAACAGAGGGGCCTCTCTGGATTTCTGTATCCCTGGTTTA

AACAAAGGCCCCAGCAAGCTGAGCCACCAAAGCTCTGGGGATCATGAGGA

ACAAAGGCAGAGGGAGAGCAGAGTGCTGACAGGCCAGGGCCAGAGGCCGC
                                                →
AGGGCTATAAAGAGGAGGGCCACAGAGCAAGTGGTACCAGATGGAGACCC
                                  +45
AGGCTGAGCAGCAGGAGCTGGGTGAGTAAGAGCT

Fig. 19

GATCTAGCCTCAGCTCTACGCGCCTGGCGCCCTCCCTACGCGGGCGTCCC

CGACTCCCGCGCGCGTTCAGGCTCCGGGTTGGGAACCAAGGAGGGGGAGG

GTGGGTGCGCCGACCCGGAAACACCATATAAGGAGCAGGAAGGATCCCCC

GCCGGAACAGACCTTATTTGGGCAGCGCCTTATATGGAGTGGCCCAATAT

GGCCCTGCCGCTTCCGGCTCTGGGAGGAGGGGCGAACGGGGGTTGGGGCG

GGGGCAAGCTGGGAACTCCAGGAGCCTAGCCCACTCATGGCAGAGACTTC

TGTCCTCACCCCCTAGCTGCTCTGAGAGATTAAGAAAGCCAAGGCCTGCA

GCAGCCAGCCATGCCCACAACAGAGGGGCCTCTCTGGATTTCTGTATCCC

TGGTTTAAACAAAGGCCCCAGCAAGCTGAGCCACCAAAGCTCTGGGGATC

ATGAGGAACAAAGGCAGAGGGAGAGCAGAGTGCTGACAGGCCAGGGCCAG

AGGCCGCAGGGCTATAAAGAGGAGGGCCACAGAGCAAGTGGTACCAGATG

GAGACCCAGGCTGAGCAGCAGGAGCTGGGTGAGTAAGAGCT

Fig. 20A

SEQUENCE LISTING

<160> NUMBER OF SEQ ID NOS: 13

<210> SEQ ID NO 1
<211> LENGTH: 704
<212> TYPE: DNA
<213> ORGANISM: Rattus sp.
<220> FEATURE:
<223> OTHER INFORMATION: EGR promoter

<400> SEQUENCE: 1

```
gatctagcct cagctctacg cgcctggcgc cctccctacg cgggcgtccc cgactcccgc      60
gcgcgttcag gctccgggtt gggaaccaag gaggggagg gtgggtgcgc cgacccggaa     120
acaccatata aggagcagga aggatccccc gccggaacag accttatttg ggcagcgcct    180
tatatggagt ggcccaatat ggccctgccg cttccggctc tgggaggagg ggcgaacggg    240 ggttgggcg ggggcaagct gggaactcca ggagcctagc ccgggaggcc actgccgctg    300
ttccaatact aggctttcca ggagcctgag cgctcagggt gccggagccg gtcgcaggt    360 ggaagcgccc accgctcttg gatgggaggt cttcacgtca ctccgggtcc tcccggtcgg    420
tccttccata ttagggcttc ctgcttccca tatatggcca tgtacgtcac ggcggaggcg    480
ggcccgtgct gtttcagacc cttgaaatag aggccgattc ggggagtcgc gagagatccc    540
agcgcgcaga acttgggag ccgccgccgc gattcgccgc cgccgccagc ttccgccgcc    600
gcaagatcgg cccctgcccc agcctccgcg gcagccctgc gtccaccacg ggccgcggcc    660
accgccagcc tgggggccca cctacactcc ccgcagtgtg agct                     704
```

<210> SEQ ID NO 2
<211> LENGTH: 303
<212> TYPE: DNA
<213> ORGANISM: Homo sapiens
<220> FEATURE:
<223> OTHER INFORMATION: MIP promoter

<400> SEQUENCE: 2

```
gatctttcca gtcctgctgt tcttcacccc cacttctcgt agtctctctt gctgtgaccc      60
caatcccacc ctcactgcca tggctctctc ggctcatctc ccagttgaga aaggcgggaa     120
aatccagcat ttttaccatg taggggaggg gacttagccc tccacagctg tgaagggggtt    180
```
(Note: reading carefully)
```
gatctttcca gtcctgctgt tcttcacccc cacttctcgt agtctctctt gctgtgaccc      60
caatcccacc ctcactgcca tggctctctc ggctcatctc ccagttgaga aaggcgggaa     120
aatccagcat ttttaccatg taggggaggg gacttagccc tccacagctg tgaagggggtt    180 aagaggctgg gcctgctacc tcagcctgcc cctcccaggg attaggagtc ctctataaag    240
gggactgtcc acccagacaa ggccatgggg gtagcaggga cccaggcact gtgaccatga    300
gct                                                                   303
```

<210> SEQ ID NO 3
<211> LENGTH: 585
<212> TYPE: DNA
<213> ORGANISM: Artificial Sequence
<220> FEATURE:
<223> OTHER INFORMATION: Description of Artificial Sequence: Composite promoter
<223> OTHER INFORMATION: Comp1 - rat EGR and human MIP promoter

<400> SEQUENCE: 3

```
gatctagcct cagctctacg cgcctggcgc cctccctacg cgggcgtccc cgactcccgc      60
gcgcgttcag gctccgggtt gggaaccaag gaggggagg gtgggtgcgc cgacccggaa     120
acaccatata aggagcagga aggatccccc gccggaacag accttatttg ggcagcgcct    180
tatatggagt ggcccaatat ggccctgccg cttccggctc tgggaggagg ggcgaacggg    240
ggttggggcg ggggcaagct gggaactcca ggagcctagc ccgatctttc cagtcctgct    300
gttcttcacc cccacttctc gtagtctctc ttgctgtgac cccaatccca ccctcactgc    360
catggctctc tcggctcatc tcccagttga gaaaggcggg aaaatccagc attttacca    420 tgtaggggag gggacttagc cctccacagc tgtgaagggg ttaagaggct gggcctgcta    480
cctcagcctg cccctcccag ggattaggag tcctctataa aggggactgt ccacccagac    540
aaggccatgg ggtagcagg acccaggca ctgtgaccat gagct                      585
```

<210> SEQ ID NO 4
<211> LENGTH: 384
<212> TYPE: DNA
<213> ORGANISM: Homo sapiens
<220> FEATURE:
<223> OTHER INFORMATION: beta-crystallin promoter
<223> OTHER INFORMATION: Wherein any N may be A, T, G or C

<400> SEQUENCE: 4

```
gatctcccag ggtcttaagg tcttaggaag atcccaaggt ggtgtgagga acntggagaa     60
ggacaagaga caagtactca tggcagagac ttctgtcctc accccctagc tgctctgaga    120
gattaagaaa gccaaggcct gcagcagcca gccatgccca aacagaggg gcctctctgg     180 atttctgtat ccctggttta aacaaaggcc ccagcaagct gagccaccaa agctctgggg    240
atcatgagga acaaaggcag agggagagca gagtgctgac aggccagggc cagaggccgc    300
agggctataa agaggagggc cacagagcaa gtggtaccag atggagaccc aggctgagca    360
gcaggagctg ggtgagtaag agct                                           384
```

<210> SEQ ID NO 5
<211> LENGTH: 591
<212> TYPE: DNA
<213> ORGANISM: Artificial Sequence
<220> FEATURE:
<223> OTHER INFORMATION: Description of Artificial Sequence: Composite promoter
<223> OTHER INFORMATION: Comp2 - EGR and beta-crystallin promoter

<400> SEQUENCE: 5

| | | | | | |
|---|---|---|---|---|---|
| gatctagcct | cagctctacg | cgcctggcgc | cctccctacg | cgggcgtccc | cgactcccgc | 60 |
| gcgcgttcag | gctccgggtt | gggaaccaag | gaggggagg | gtgggtgcgc | cgacccggaa | 120 |
| acaccatata | aggagcagga | aggatccccc | gccggaacga | accttatttg | ggcagcgcct | 180 |
| tatatggagt | ggcccaatat | ggccctgccg | cttccggctc | tgggaggagg | ggcgaacggg | 240 |
| ggttggggcg | ggggcaagct | gggaactcca | ggagcctagc | ccactcatgg | cagagacttc | 300 |
| tgtcctcacc | ccctagctgc | tctgagagat | taagaaagcc | aaggcctgca | gcagccagcc | 360 |
| atgcccacaa | cagaggggcc | tctctggatt | tctgtatccc | tggtttaaac | aaaggcccca | 420 |
| gcaagctgag | ccaccaaagc | tctggggatc | atgaggaaca | aaggcagagg | gagagcagag | 480 |
| tgctgacagg | ccagggccag | aggccgcagg | gctataaaga | ggagggccac | agagcaagtg | 540 |
| gtaccagatg | gagacccagg | ctgagcagca | ggagctgggt | gagtaagagc | t | 591 |

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: PCR primer
<223> OTHER INFORMATION: 5' rat EGR-1 primer

<400> SEQUENCE: 6
gaagatctag cctcagctct acgcgcct        28

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: PCR primer
<223> OTHER INFORMATION: 3' rat EGR-1 primer

<400> SEQUENCE: 7
gaagagctca cactgcgggg agtgtaggt        29

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: PCR primer
<223> OTHER INFORMATION: HSV tk 5' primer

<400> SEQUENCE: 8
ctgaattcct tgtagaagcg cgtatggc        28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: PCR primer
<223> OTHER INFORMATION: HSV tk 3' primer

<400> SEQUENCE: 9
cgcaagcttc tccttccgtg tttcagtt        28

<210> SEQ ID NO 10

```
<211> LENGTH: 28
<212> TYPE: DNA
<213> ORGANISM: Artificial Sequence
<220> FEATURE:
<223> OTHER INFORMATION: Description of Artificial Sequence: PCR primer
<223> OTHER INFORMATION: MIP 5' primer

<400> SEQUENCE: 10
gaagatctct tccagtcctg ctgttctt                                          28

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: PCR primer
<223> OTHER INFORMATION: MIP 3' primer

<400> SEQUENCE: 11
gaagagctca tggtcacagt gcctgggtc                                         29

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: PCR primer
<223> OTHER INFORMATION: human A3/A1 beta crystallin promoter 5' primer

<400> SEQUENCE: 12
gaagatctcc cagggtctta aggt                                              24

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: PCR primer
<223> OTHER INFORMATION: human A3/A1 beta crystallin promoter 3' primer

<400> SEQUENCE: 13
gaagagctct tactcaccca gctcctgc                                          28
```

SOMATIC GENE THERAPY TO SUPPRESS SECONDARY CATARACT FORMATION FOLLOWING EYE SURGERY

BACKGROUND OF THE INVENTION

This invention relates to materials and methods for the construction of recombinant viral, particularly adenoviral, delivery systems that provide lens epithelial cell type specific regulation of expression of proteins which inhibit cellular proliferation. This invention also relates to the use of these recombinant viral delivery systems for inhibiting or preventing the formation of secondary cataracts following surgical intervention on the eye.

Cataract operations are the second most frequent operation in the western world. The cataract is an affliction characterized by an opacification of the crystalline lens of the eye which reduces the visual acuity of the patient. The surgical technique currently utilized for removing cataracts consists of removing the crystalline with a small aspirator. Access to the interior of the crystalline capsule is achieved by a circular opening at the anterior face of the lens capsule. This permits the surgeon to insert a new lens, which will restore the eye's ability to focus incoming light on the surface of the retina.

Secondary cataracts constitute the most frequent complication following this operation, occurring in up to 50% of adult eyes and even more frequently following surgery of children with congenital cataracts (Nischi et al., 1986). (Surgical interventions on the eyes of rabbits also result in secondary cataract formation (100%) in the weeks following the operation (Blomstedt. et al., 1987)). Human secondary cataracts are characterized by a secondary opacification of the posterior capsule appearing in the months following surgery. They are the consequence of the stimulated proliferation at the level of the germinative epithelium of the lens, which are the only cells with division potential in the mature eye. Laser treatment, which is the accepted means of treating secondary cataracts, unfortunately risks additional complications, the most notable of which is detachment of the retina (Salvenson et al., 1991).

SUMMARY OF THE INVENTION

In accordance with this invention is provided a replication-defective recombinant virus that can infect an eye of a patient and that contains:

an Open Reading Frame (ORF) which, when expressed in lens epithelial cells of the eye, suppresses, at the level of the germinative epithelium of the lens of the eye, cellular proliferation which is stimulated by eye surgery and which would otherwise result in secondary cataract formation in the eye;

the ORF, to be expressed, being under the control of a promoter sequence which is active exclusively in human lens epithelial cells.

The preferred replication-defective recombinant virus is a replication-defective recombinant adenovirus, especially an adenovirus lacking E1a, 1b and E4 ORF 6.

The preferred ORF, to be expressed, is one of the following:

a) an ORF encoding a protein that regulates the cell cycle, especially a non-phosphorylatable retinoblastoma (Rb) gene;

b) a dominant negative mutant of an ORF encoding a protein involved in signal transduction, especially a dominant negative mutant of a RAS gene, particularly the codon 116 mutant of the human RAS gene; or c) an ORF encoding a protein which will severly disrupt DNA replication in human lens epithelial cells, especially a thymidine kinase gene of a Herpes virus, particularly the Herpes Simplex type 1 thymidine kinase (HSTK) gene (to be used in conjunction with a treatment of the patient with acyclovir or a nucleoside analogue thereof).

The preferred promoter sequence is one of the following:

a) a promoter of a human Major Intrinsic Protein (MIP) gene, preferably the portions of the MIP gene from −259 nt to +34 nt, or b) a promoter of a human A3/A1-crystallin gene, preferably the portions of the -crystallin gene from −345 nt to +45 nt, or preferably c) a composite promoter comprising either the MIP promoter or the -crystallin promoter or portions thereof, in combination with elements of an early growth response gene promoter such as the rat Early Growth Response-1 (EGR-1) gene promoter from −518 nt to −236 nt of the EGR-1 gene.

Also in accordance with this invention are provided:

a) purified and isolated DNA sequences of the composite EGR-1/MIP and composite EGR-1/-crystallin promoters and b) vectors for the formation of replication-defective recombinant viruses containing the gene, to be expressed, under the control of the promoter sequence which is expressed exclusively in human lens epithelial cells.

Further in accordance with this invention is provided a method for the treatment of an eye, undergoing eye (e.g. cataract) surgery, in order to reduce the incidence of cellular proliferation in the eye following the eye surgery, and thereby prevent the formation of secondary cataracts, comprising the step of:

treating the eye with the replication-defective recombinant virus, particularly adenovirus, of this invention, preferably during the eye surgery.

BRIEF DESCRIPTION OF THE FIGURES

FIG. 4 is the DNA sequence of the rat EGR-1 promoter (SEQ ID NO:1) of Example 1.

FIG. 9 is the DNA sequence of the human MIP promoter (SEQ ID NO:2) of Example 2.

FIG. 14A is the DNA sequence (SEQ ID NO:3) of the composite 1 promoter of pxcComp1 of Example 3.

FIG. 19 is the DNA sequence (SEQ ID NO:4) of the human α-crystallin promoter of Example 4.

FIG. 20A is the DNA sequence (SEQ ID NO:5) of the composite 2 promoter of pxcComp2 of Example 5.

DETAILED DESCRIPTION OF THE INVENTION

Figure 1:
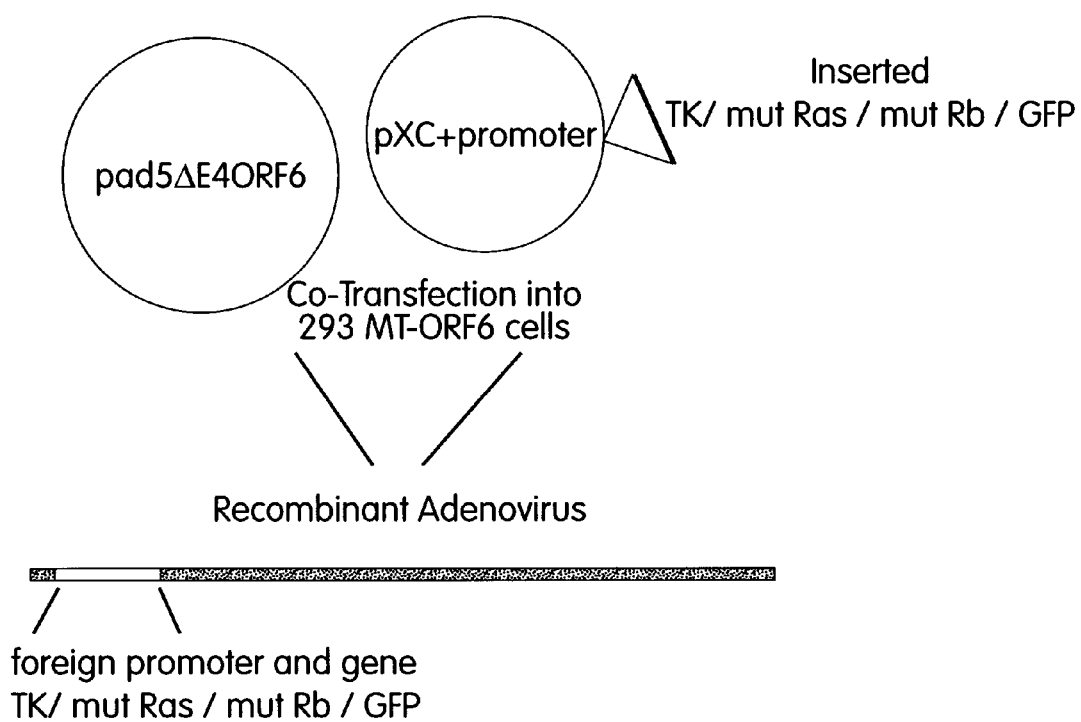
FIG. 1 shows schematically the two-step process for the construction of a replication-defective recombinant adenovirus in accordance with this invention.

This invention involves the use of a replication-defective recombinant virus, preferably an adenovirus, to reduce the incidence of cellular proliferation following surgical intervention on the eye of mammals, especially humans. In particular, replicative-defective recombinant adenoviral vectors are used to deliver ORF whose encoded proteins suppress, at the level of the germinative epithelium of the lens of the eye, cellular proliferation that is stimulated by the eye surgery and that would otherwise result in secondary cataract formation.

The particularly preferred replication-defective recombinant virus is a recombinant adenovirus lacking E1a, 1b and E4 ORF 6. However equivalents of this virus can also be used, such as HIV-derived replication-defective retroviruses and Adeno-associated viruses (Kearns et al., 1996; Liu, ML. et al., 1996; Russ et al., 1996; Xiao and Samulski, 1996), as well as non-viral equivalents such as liposomes (Hangai et al., 1996).

The preferred ORF, to be expressed, is one of the following:

a) an ORF encoding a protein that regulates the cell cycle, especially a non-phosphorylatable retinoblastoma (Rb) gene;

b) a dominant negative mutant of an ORF encoding a protein involved in signal transduction, especially a dominant negative mutant of a human RAS gene (Kaplan, 1994; Sung et al., 1996), particularly the codon 116 mutant of the human RAS ORF; other examples of such ORFs are the p16 and p21 genes (Kamb et al., 1994; Wu et al., 1996); or c) an ORF encoding a protein which will severely disrupt DNA replication in human lens epithelial cells, especially a thymidine kinase gene of the Herpes virus family, such as the the Herpes Simplex type 1 virus or Varicella zoster, or the UL-97 gene of Cytomegalovirus which encodes a protein kinase (to be used in conjunction with a treatment of the patient with acyclovir or a nucleoside analogue thereof).

The ORF, to be expressed, is placed under the control of a tissue-specific promoter so that the expression of the ORF occurs uniquely in lens epithelial cells. In this regard, precise expression of the desired ORF in lens epithelial cells is preferably achieved by the use of promoter elements of the human MIP gene (particularly from −259 nt (nucleotide) to +34 nt), promoter elements of the human beta-crystallin gene (particularly from −345 nt to +45 nt) or promoter elements of both genes. Other lens epithelial cell-specific promoter can also be used, such as the promoters of the human alpha, gamma, delta or epsilon-crystallin genes (Chepelinsky et al.,1991; Piatigorsky, 1989; Kondoh et al., 1988).

The promoters of the endogenous MIP and β-crystallin genes, like the other lens epithelial cell specific promoters, are methylated in all cell types except differentiated lens epithelial cells. This methylation renders the promoters inactive. The divisional event that precedes differentiation is accompanied by a de-methylation of the lens cell specific promoters. It has been demonstrated that non-methylated lens specific promoters are active in the germinal cells (Peek et al., 1991). Recombinant adenoviruses of this invention are therefore produced in the presence of 5-aza-2'-deocytidine to ensure that no methylation of the lens specific promoters takes place during production of the recombinant virus.

It is particularly preferred that rapid ORF expression, following surgery, be achieved by the presence of elements of the promoter of an early growth response gene or an "immediate early gene" (Kiessling and Gass, 1993; Weichselbaum et al., 1994), preferably cis rat EGR-1 elements, in composite promoter constructs of this invention which also contain portions of the β-crystallin or MIP promoter. Such composite promoter constructs of this invention are provided with:

a) first elements intended to provide rapid expression of the ORFs, to be expressed, upon mitotic signaling, with subsequent decay of expression of the ORFs; these first elements are not believed to exhibit tissue specificity; and b) second elements comprising the promoter of the MIP gene and /or the promoter of the -crystallin gene; these second elements ensure exquisite tissue specific expression yet are less rapidly induced to promote expression following entry into lens epithelial cells.

The construction of a replicative-defective recombinant adenovirus in accordance with this invention takes place in two steps as schematically shown in FIG. 1.

In the first step, the ORF, to be expressed, is cloned downstream of a particular promoter and of an intron and upstream of the poly A site into the polylinker of a pXC plasmid (FIG. 3) which contains the left end of adenovirus (nucleotides 1–5788 with a 2700 nt deletion of the E-1a–1b region between nucleotide positions 358 and 3328 in Genebank Accession no. M73260).

Figure 2:
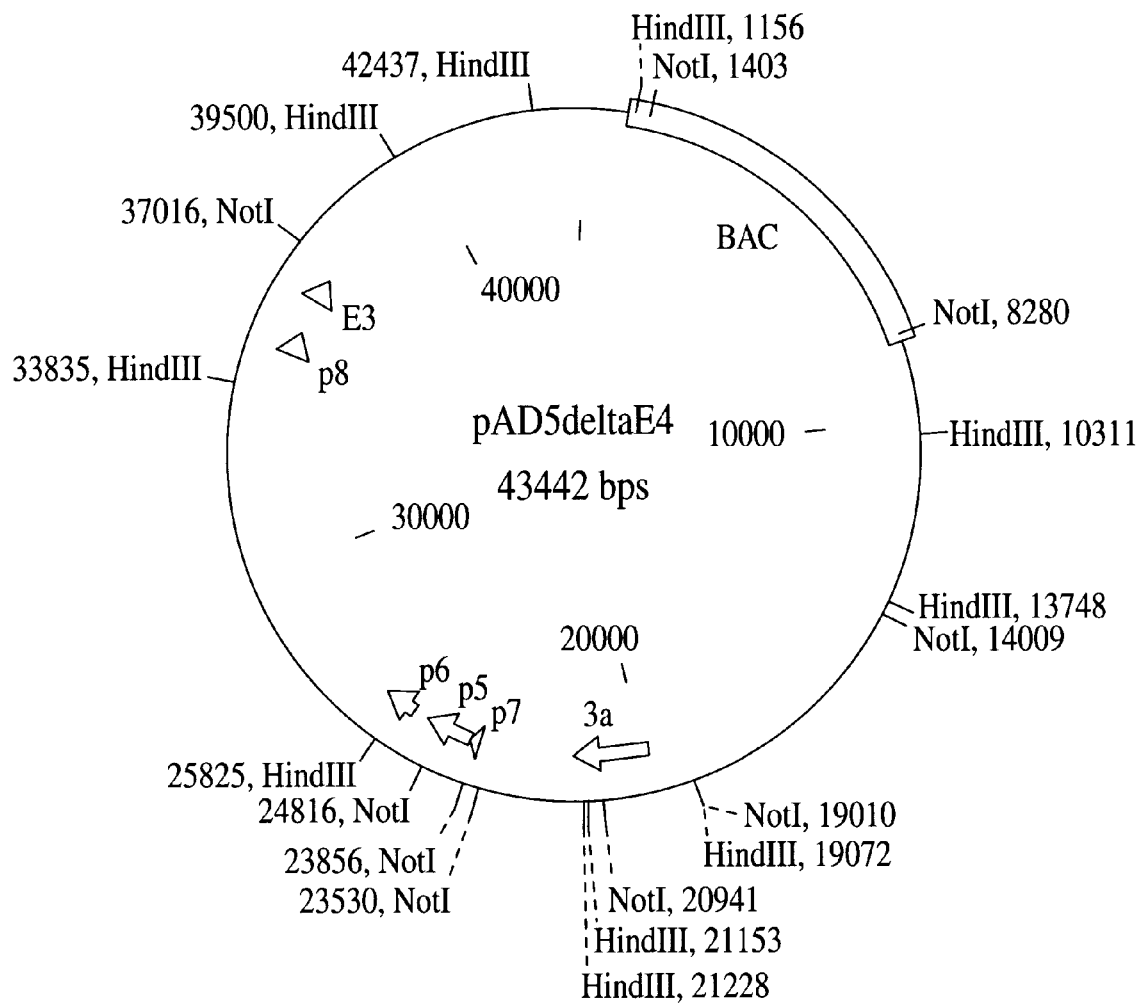
FIG. 2 is a restriction map of plasmid pad5ΔE4ORF6, used in the process shown in FIG. 1 and described in Example 8.

The resulting pXC plasmid (recombinant 1) is then co-transfected with a modified pJM17 plasmid, shown in FIG. 2, into a modified 293 cell line (Graham et al., 1977), which is a transformed human cell line that constitutively expresses Ad5 E1 proteins and can be induced to synthesize the E4 ORF 6 protein. Due to homologous recombination between the pXC plasmid with its adenovirus left-end construct, the pad5ΔE4ORF6 plasmid, and the helper (complementing) function of the E1 and E4 ORF 6 proteins provided by the 293/MTE4ORF6 cells, a replication-defective recombinant adenovirus is produced and packaged. The packaged recombinant adenovirus produced by the transfected 293/MTE4ORF6 cells has a deleted E-1a-1b region that is replaced by the promoter and ORF, of interest, initially inserted into the recombinant 1 plasmid. Plaque purifications (three times) and analysis of resulting recombinant virus are carried out to verify the sequence of the resulting recombinant virus. The recombinant adenovirus is incapable of replicating in cells other than modified 293 cells and thus constitutes simply a delivery system for the protein encoded by the ORF, to be expressed.

A rabbit model system, exhibiting essentially 100% secondary cataract formation in the 2–3 weeks following surgical intervention of the eye, can be used, as described below, to evaluate the efficiency of suppression of lens epithelial cell proliferation by the recombinant adenovirus vectors of this invention.

The following three ORFs are independently expressed in replication-defective recombinant adenoviral vectors:

1. a non-phosphorylatable Rb ORF
2. a dominant negative mutant (at amino acid position 116) of the human RAS ORF and
3. a Herpes Simplex type 1 thymidine kinase ORF.

Control of expression in the recombinant adenoviral vectors is with one of the following four promoter sequences:

1. a human Major Intrinsic Protein (MIP) gene promoter,
2. a first composite promoter containing elements of the rat Early Growth Response -1 (EGR-1) gene promoter (from −518 nt to −236 nt) and the human Major Intrinsic Protein (MIP) gene promoter (from −259 nt to +34 nt)
3. a human βA3/A1-crystallin promoter (−345 nt to +45 nt) and
4. a second composite promoter containing elements of the EGR-1 promoter (from −518 nt to −236 nt) and the β-crystallin promoter (−345 nt to +45 nt).

Correct expression of recombinant adenoviruses containing lens epithelial cell specific promoters is verified in in vitro cultures of lens capsular sacs of pig eyes which have been operated upon. The germinal epithelial cells of pig eyes capsular sacs, that have undergone cataract surgery, proliferate in a manner analogous to secondary cataract formation (Liu, C. et al., 1996; Wormstone et al., 1997).

A replication-defective recombinant adenovirus for each promoter-ORF construct is made by co-transfection of first stage vectors with the modified pJM17 plasmid lacking E4 ORF 6 into the modified 293 cell line with metal inducible expression of E4 ORF 6 protein.

In the next step, rabbit lens capsular sacs are infected at the time of surgical intervention with an adenovirus transformed with the coding sequence for the Green Fluorescent Protein (GFP), in order to determine the efficiency and specificity of ORF delivery and expression in accordance with the invention at different multiplicities of infection (MOIs). Infection of the eyes during surgery can be carried out in a conventional mannner in accordance with this invention, but preferably, the eyes are infected by introducing the recombinant adenoviral vector at the final stage of the surgery, that is when the chamber is refilled with sterile physiological solution. Once appropriate MOIs have been determined, the duration of foreign ORF expression is evaluated. Subsequently, the efficiency of suppression of cellular proliferation is analyzed in operated eyes, using the recombinant adenoviruses containing either the non-phosphorylatable Rb ORF, the dominant negative RAS ORF or the HSTK ORF (in conjunction with a treatment with acyclovir or a nucleoside analogue thereof).

Green Fluorescent Protein (GFP) is an auto-fluorescing protein expressed in jelly fish. The advantage of this protein is that its expression can be easily detected without the addition of any other components, such as is necessary for many other marker ORF systems. A source of the GFP ORF (FIG. 5) for the recombinant adenovirus construct of this invention is the pxcEGR-GFP plasmid shown in FIG. 5A. The protein encoding sequence is modified in two respects: i) the codon usage is modified to be translated optimally in mammalian cells and ii) the wavelength necessary to excite the protein to fluoresce is modified to be in the near visible, as opposed to the far ultraviolet, as is the case for the native jellyfish protein.

A retinoblastoma (Rb) cDNA clone is obtainable from Dr. Hamel in the department of Medical Genetics at the University of Toronto (Hamel et al., 1992). The clone contains eight point mutations at both serine and threonine residues, thus rendering the encoded retinoblastoma protein non-phosphorylatable. (See FIG. 7.) Over-expression of this Rb protein is known to result in cell cycle arrest in the G1 phase of the cell cycle (Hamel et al., 1992; Chang et al., 1995).

A Harvey RAS ORF construct (FIG. 6), containing a dominant negative mutation at codon 116 (tyrosine replacing the wild-type asparagine at amino acid position 116), is obtainable from Dr. Kuzumaki of Hokkaido University, Japan.

Figure 8:
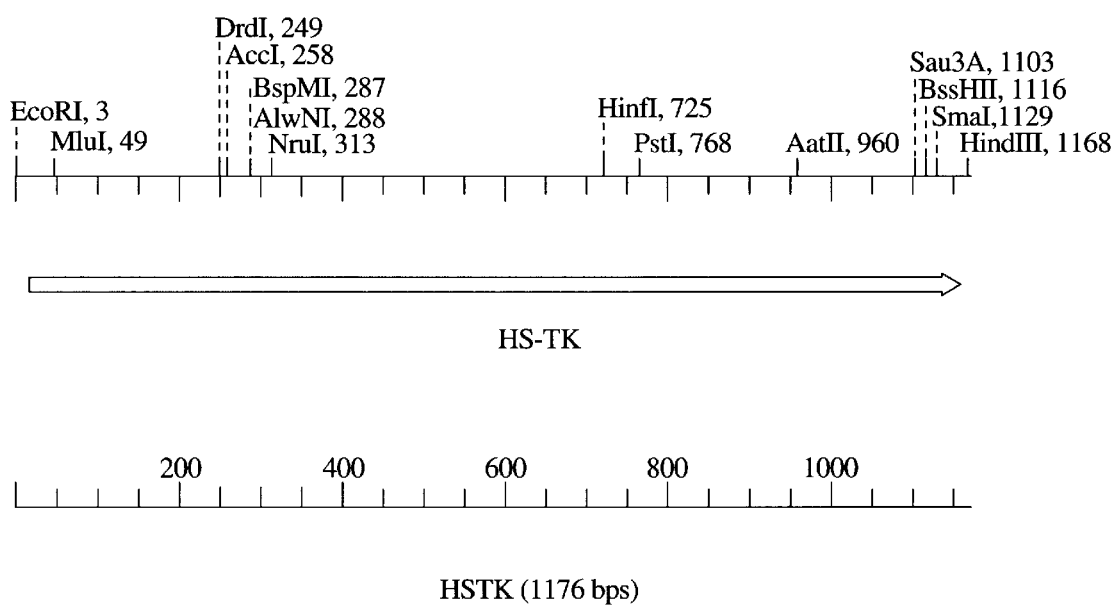
FIG. 8 is a restriction map of the HSTK ORF of Example 1.

A ORF encoding Herpes Simplex type 1 thymidine kinase (HSTK), as shown in FIG. 8, is known from Waldman et al. (1983).

An evaluation of a stimulated immune response directed against adenovirus in infected rabbits is undertaken to determine whether it is possible to re-infect with recombinant virus without neutralization by the immune system. In principle, the interior of the eye should be "protected" from the immune system, and multiple infections with replication-defective recombinant adenoviral vectors should render suppression of lens epithelial cell proliferation more efficient than a single infection at the time of the operation.

The surgical technique used on the rabbits is identical to that used in the human cataract operation described above. This animal system thus constitutes an ideal model to demonstrate the effectiveness of somatic gene therapy in suppressing post-operative cellular proliferation, causing secondary cataract. Any immune reaction, engendered by infection with a recombinant adenoviral vector, is easily assessed by analysing "infected" rabbit sera for stimulated response to adenovirus capsid proteins. In the absence of an immune reaction, the relative efficiency of multiple infections of replication-defective recombinant adenovirus vectors is then evaluated.

When the recombinant adenovirus of this invention contains a thymidine kinase ORF of a Herpes virus, particularly the Herpes Simplex type 1 thymidine kinase (HSTK) ORF, the patient is also treated with acyclovir or a nucleoside analogue structurally related to acyclovir, such as gancyclovir, famcyclovir and valacyclovir, preferably with acyclovir (Clive et al., 1983). Acyclovir and its nucleoside analogues are phosphorylated by the Herpes thymidine kinase and subsequently incorporated into host cell DNA. Once incorporated, they function as chain terminating nucleotides, and thus, cells expressing the viral thymidine kinase and incorporating the phosphorylated analogue are specifically targeted. There is no reported toxicity of acyclovir at the concentrations appropriate for this use, and it can be given orally or by eye drops to the patient before, during or after surgery.

The Examples which follow illustrate the invention.

EXAMPLE 1
Construction of an Adenovirus First Stage Vector (Recombinant 1) Containing Elements of the Rat EGR-1 (Early Growth Response) Gene Promoter Amplification of the rat EGR-1 gene promoter (shown in FIG. 3) is accomplished by PCR. A 5' oligonucleotide corresponding to −538 nt to −518 nt of the transcription start site containing a synthetic Bgl II site is used in conjunction with a 3' oligonucleotide complementary to +136 nt to +156 nt with a synthetic Sac I site. The conditions of PCR are: 20 picomoles of each primer, 50 uM dNTPs, 200 ng rat DNA, 4% formamide (recrystalised), 1,5 mM MgCl in 100 I. The initial cycle is 97° for 2 ½ minutes, 72° for 5 minutes (add enzyme) 35 cycles of 95° C.-30 seconds, 63° C.-40 seconds, 72° C. 60 seconds.

```
5' primer   Bgl II                           (SEQ ID NO:6)
GA AGATCT   AGC CTC AGC TCT ACG CGC CT
                                    EGR 3'-primer   Sac I                            (SEQ ID NO:7)
GAA GAGCTC  ACA CTG CGG GGA GTG TAG GT
                                   EGR
```

The resulting 674 nt product is cleaved with Bgl II and Sac I and cloned into the Bgl II-Sac I sites of PSL 1180 (Pharmacia), and M13 forward and reverse primers are used to verify the sequence of the cloned rat EGR-1 promoter. The Bgl II-Sac I fragment of the resulting plasmid, pSL1180-EGR, is then excised and cloned into the Bgl II-Sac I sites of a CMV promoter deleted pCiNeo vector (Promega). This cloning is verified by digestion with Sma I and Nru I. The resulting plasmid, pEGRiNeo, is then cleaved with Bgl II and Fsp I. The resulting 1435 nt fragment, containing the rat EGR-1 promoter, an intron, a multicloning site and a polyA addition site, is then cloned into the Bam HI-Hpa I sites of pXC15–18 (FIG. 3; Schaak, personal communication). The resulting clone, pxcEGR, is verified by digestion with numerous restriction enzymes. A restriction map of pxcEGR is given in FIG. 4.

The following four protein coding sequences are cloned into the pxcEGR vector to form different recombinant 1 adenoviral vectors: Green Fluorescent Protein (GFP), dominant negative RAS, a non-phosphorylatable retinoblastoma (Rb) and a Herpes Simplex type 1 thymidine kinase (HSTK) ORF. Described below are the steps by which the appropriate cloning is accomplished.

Figure 5:
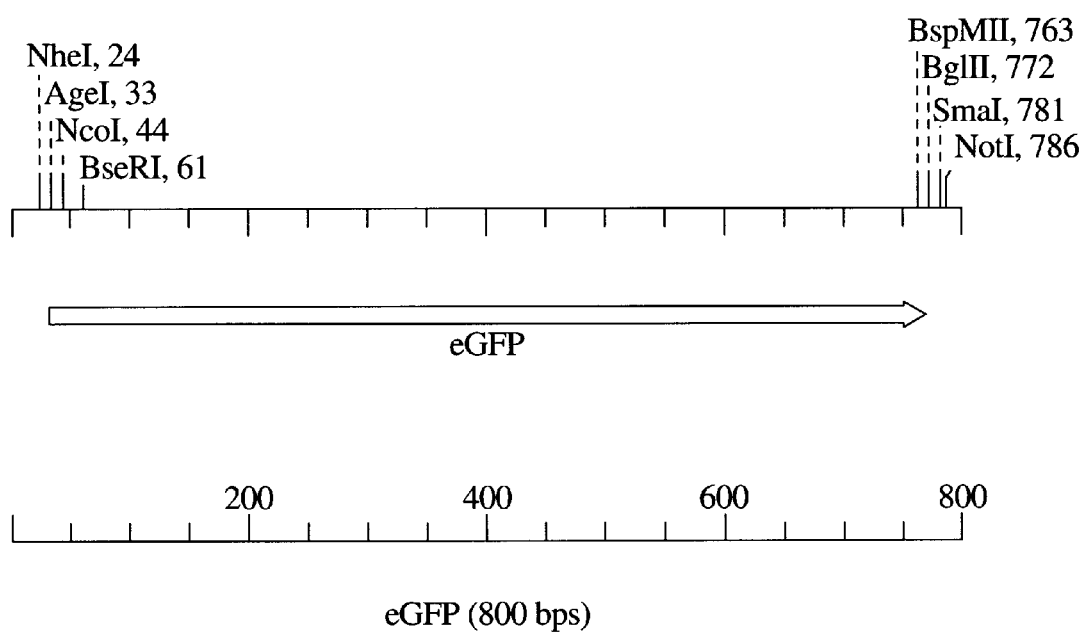
FIG. 5 is a restriction map of the GFP ORF of Example 1.
Figure 5A:
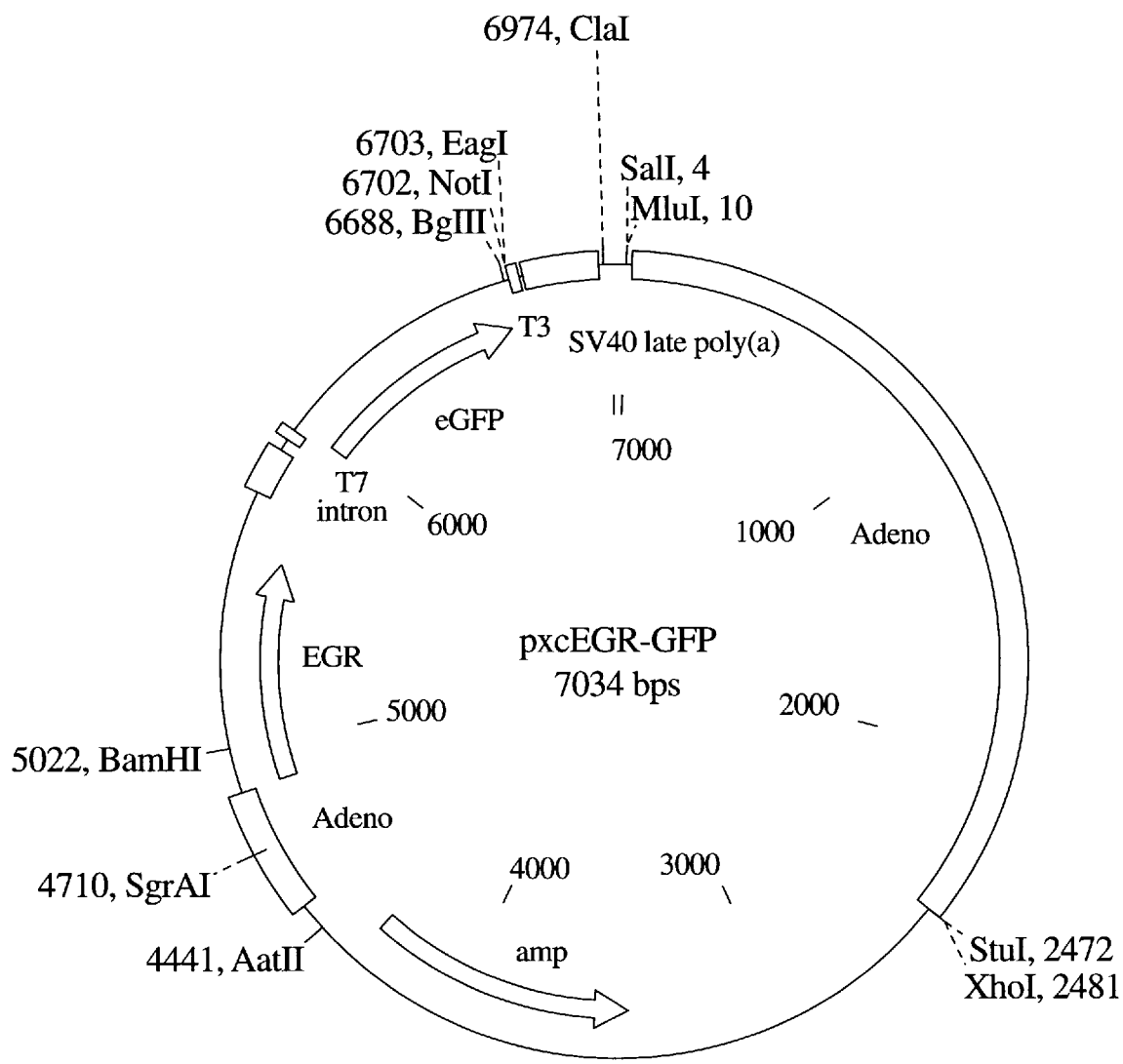
FIG. 5A is a restriction map of plasmid pxcEGR-GFP of Example 1.

GFP:

A 716 nt Nhe I-Sal I fragment encoding the Greeen Fluorescent Protein (GFP) is isolated from peGFP-C1 (Clontech) and cloned into the Nhe I, Sal I sites of pxcEGR. Sequencing of the cloning junctions and of the GFP DNA insert is accomplished with T3 and T 7 primers. FIG. 5 is a restriction map of the GFP ORF, and FIG. 5A is a restriction map of the resulting plasmid, pxcEGR-GFP.

Figure 6:
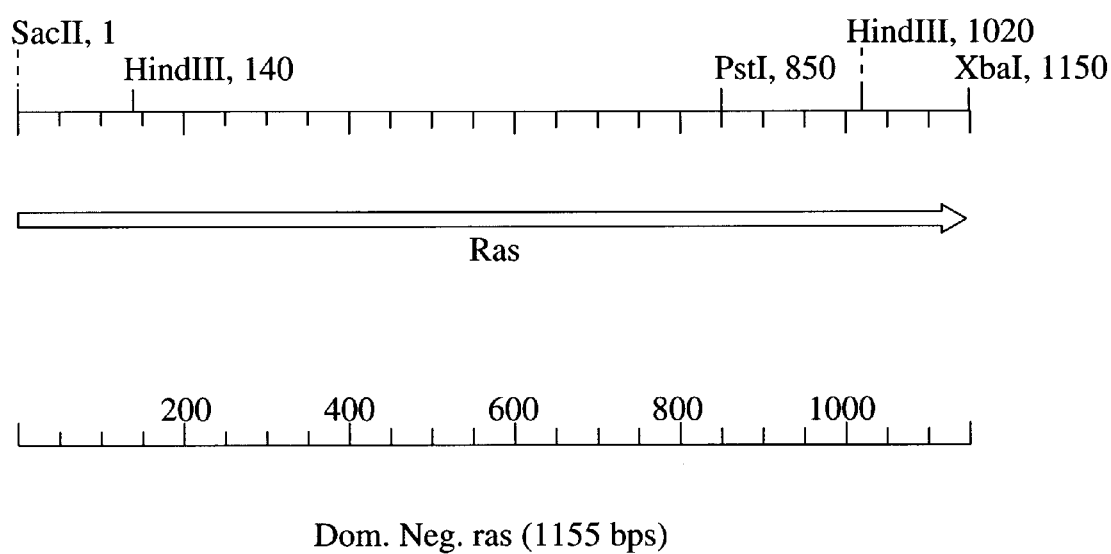
FIG. 6 is a restriction map of the dominant negative human RAS ORF of Example 1.
Figure 6A:
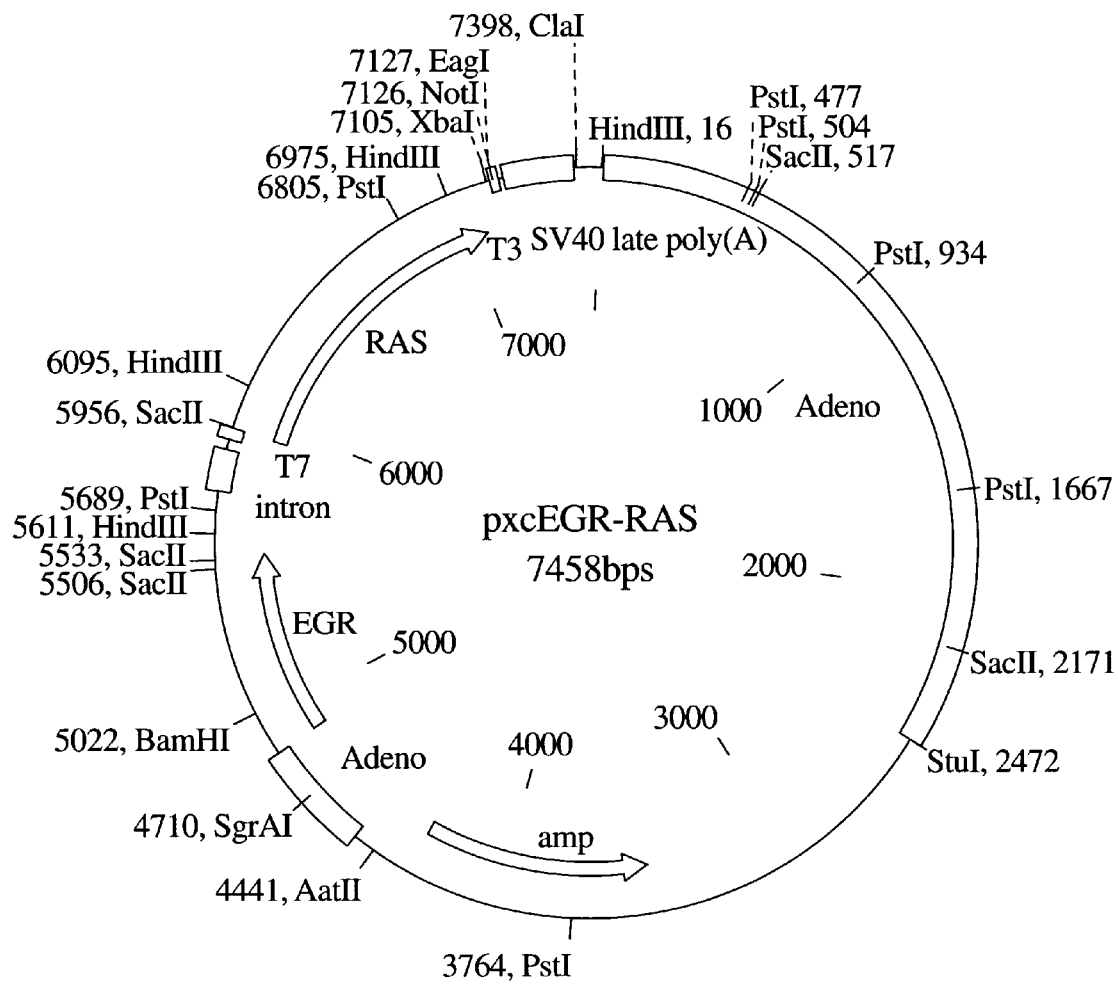
FIG. 6A is a restriction map of plasmid, pxcEGR-RAS, of Example 1.

Dominant negative RAS:

A Sac II (blunted by a Klenow fill-in reaction)-Xba I fragment of dominant negative ras cDNA, obtained from Dr. Kuzumaki, is cloned into the Nhe I (blunted by a Klenow fill-in reaction)-Xba I sites of pxcEGR. The correct clone is initially verified by restriction enzyme mapping. Sequencing of the cloning junctions and of the ras cDNA insert are performed with T3 and T 7 primers. FIG. 6 is a restriction map of the dominant negative RAS ORF, and FIG. 6A is a restriction map of the resulting plasmid, pxcEGR-RAS.

Figure 7:
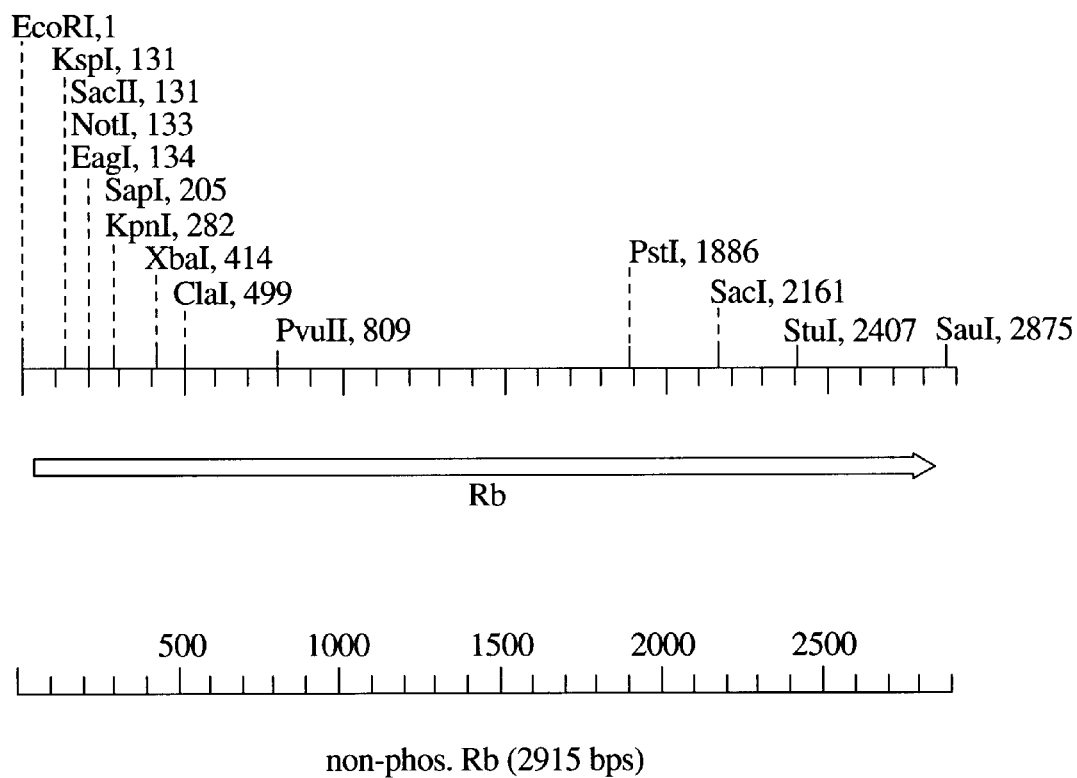
FIG. 7 is a restriction map of the Rb ORF of Example 1.
Figure 7A:
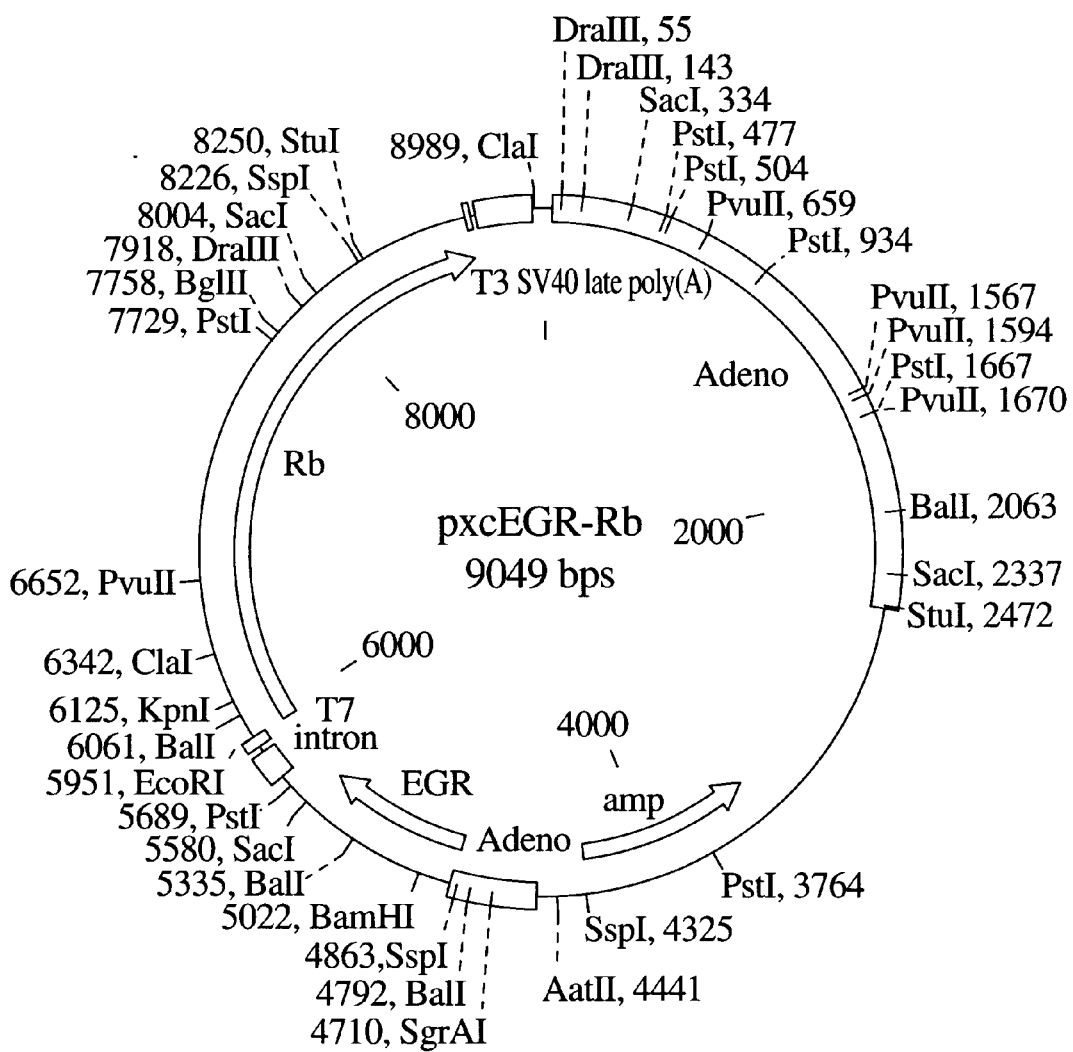
FIG. 7A is a restriction map of plasmid, pxcEGR-Rb, of Example 1.

Rb:

A 2768 nt Eco RI-Sau I (Klenow fill-in blunted) fragment from pECE34 is ligated into the Eco RI-Not I (Klenow fill-in blunted) sites of pxcEGR. The correct clone is initially identified by Sac I digestion. Sequencing of the cloning junctions and of the non-phosphorylatable Rb cDNA insert are performed with T3 and T 7 primers. FIG. 7 is a restriction map of the non-phosphorylated Rb ORF, and FIG. 7A is a restriction map of the resulting plasmid, pxcEGR-Rb.

HSTK:

A 1176 nt fragment of the Herpes Simplex type 1 thymidine kinase ORF is amplified by PCR using primers containing synthetic restriction enzyme sites, a Eco RI at the 5' end and a Hind III site at the 3' end. The ORF is amplified by PCR, using the following two primers:

5'-primer (SEQ ID NO:8) CTGAATTCCTTGTA-GAAGCGCGTATGGC

3'-primer CGCAAGCTTCTCCTTCCGTGTTTCAGTT

Figure 8A:
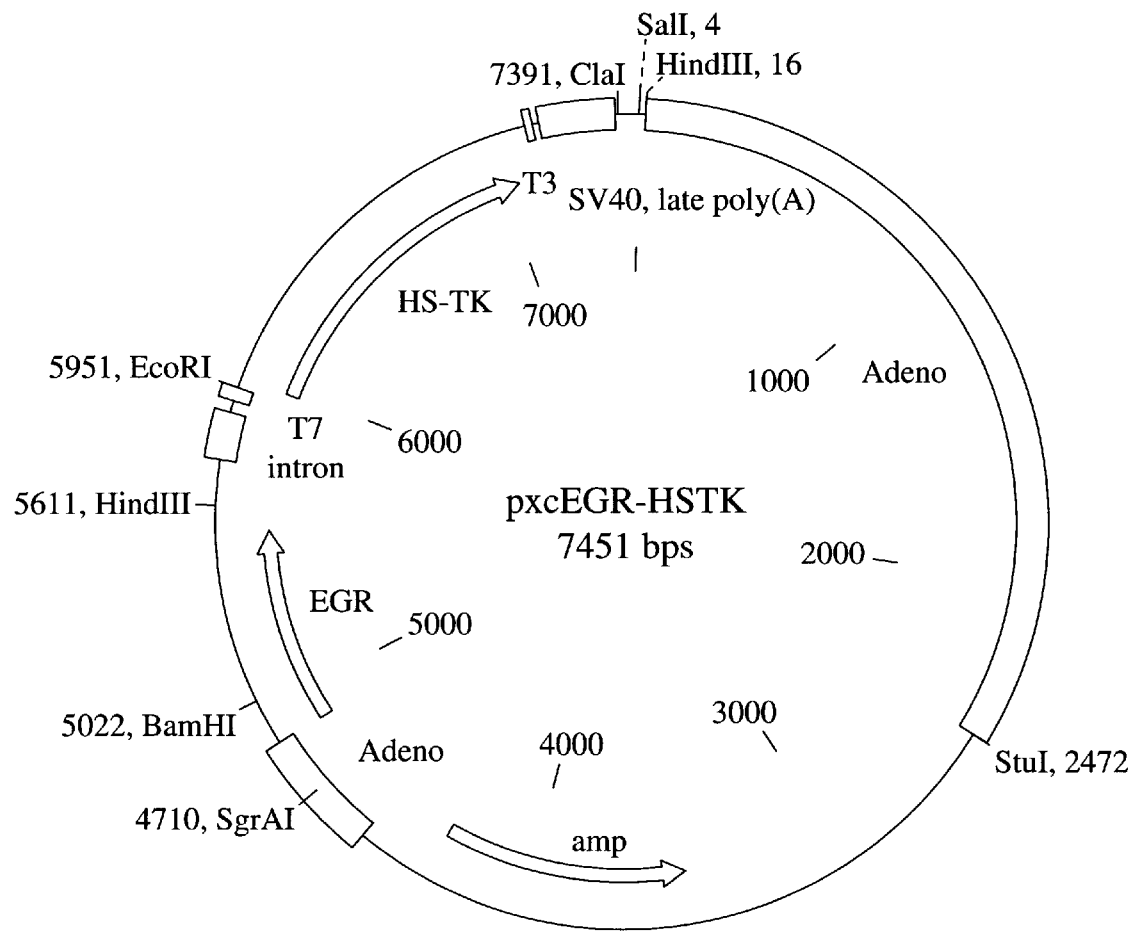
FIG. 8A is a restriction map of plasmid, pxcEGR-HSTK, of Example 1.

The thermal profile is 94° C., 5'; 58° C. 2'30; 72° C., 2': 1×; 94° C., 30 "; 58° C., 1'30"; 72° C., 2': 30×; 72° C., 6': 1×. Standard PCR buffer conditions are employed. The amplified DNA fragment is cloned into the Eco RI-Hind III sites of Bluescript vector (Stratagene). The sequence is verifed with T3 and T7 primers. This fragment is cut with Hind III, rendered blunt by a Klenow fill-in reaction, and digested with Eco RI. This fragment is then cloned into the Eco RI-Not I (blunted) sites of pxcEGR. FIG. 8 is a restriction map of the Herpes Simplex type 1 thymidine kinase ORF, and FIG. 8A is a restriction map of the resulting plasmid, pxcEGR-HSTK.

Figure 9A:
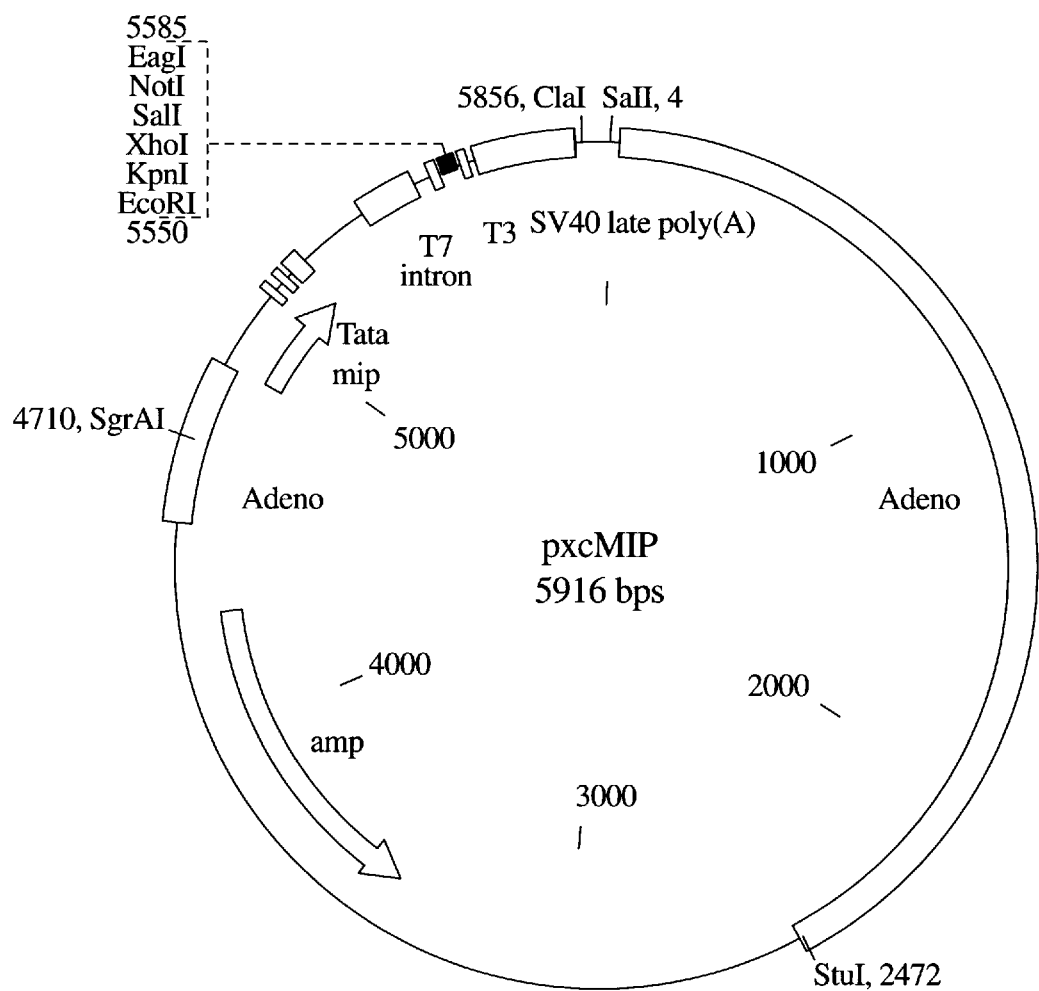
FIG. 9A is a restriction map of plasmid, pxcMIP, of Example 2.

EXAMPLE 2
Construction of an Adenovirus First Stage Vector (Recombinant 1) Containing Elements of the MIP (Major Intrinsic Protein) Gene Promoter Amplification of the human MIP gene promoter (shown in FIG. 9) is accomplished by PCR. A 5' oligonucleotide corresponding to −259 nt to −239 nt of the transcription start site containing a synthetic Bgl II site at its 5' end is used in conjunction with a 3' oligonucleotide complementary to +14 nt to +34 nt with a synthetic Sac I site. The conditions of PCR are : MIP PCR, one cycle with a 63 ° C. annealing and then a two step cycle of 94 and 70° C. for 30 cycles. Standard PCR buffer conditions are employed.

```
5'-primer   Bgl II                              (SEQ ID NO:10)
GA AGATCT   CTT CCA GTC CTG CTG TTC TT
                                    MIP 3'-primer   Sac I                               (SEQ ID NO:11)
GAA GAGCTC  ATG GTC ACA GTG CCT GGG TC
                                    MIP
```

Figure 3:
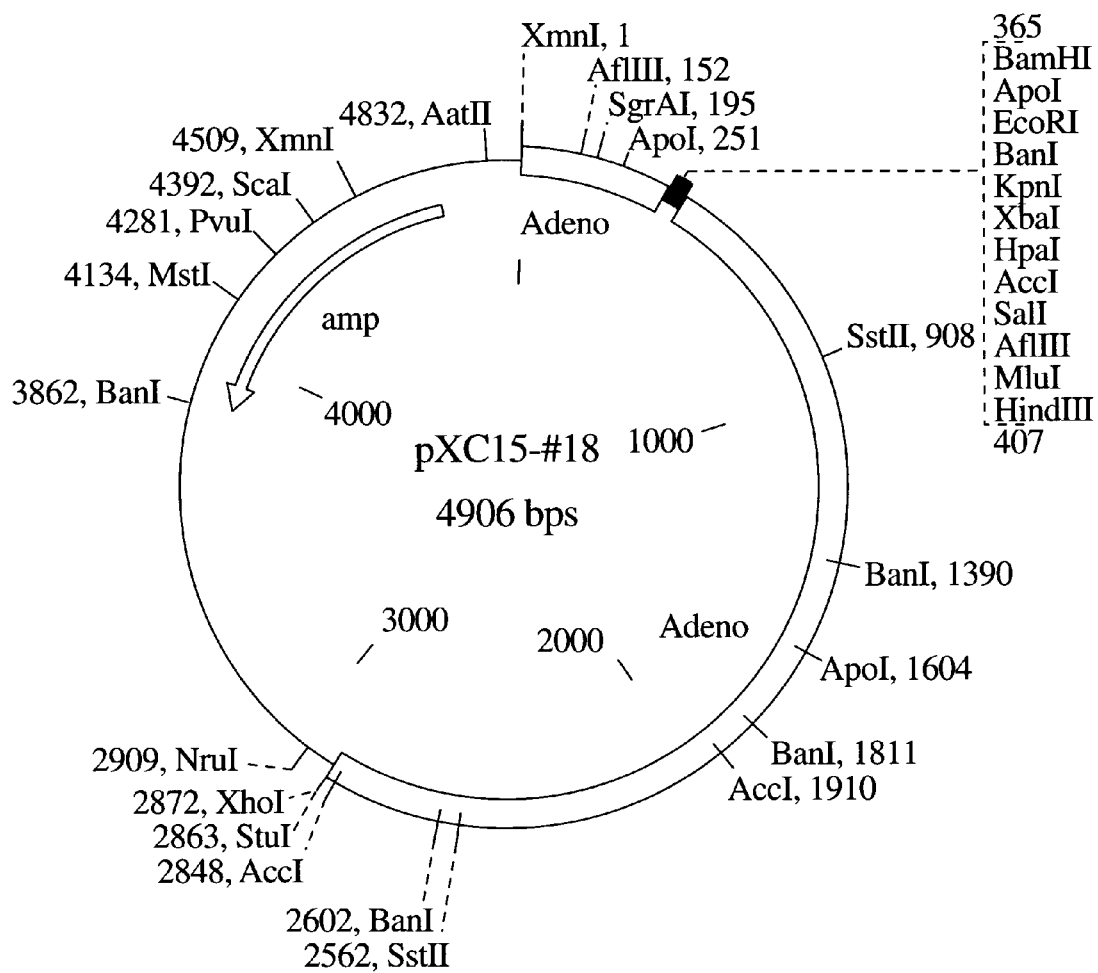
FIG. 3 is a restriction map of the plasmid pXC 15–18 used in the process shown in FIG. 1 and described in Example 8.
Figure 4A:
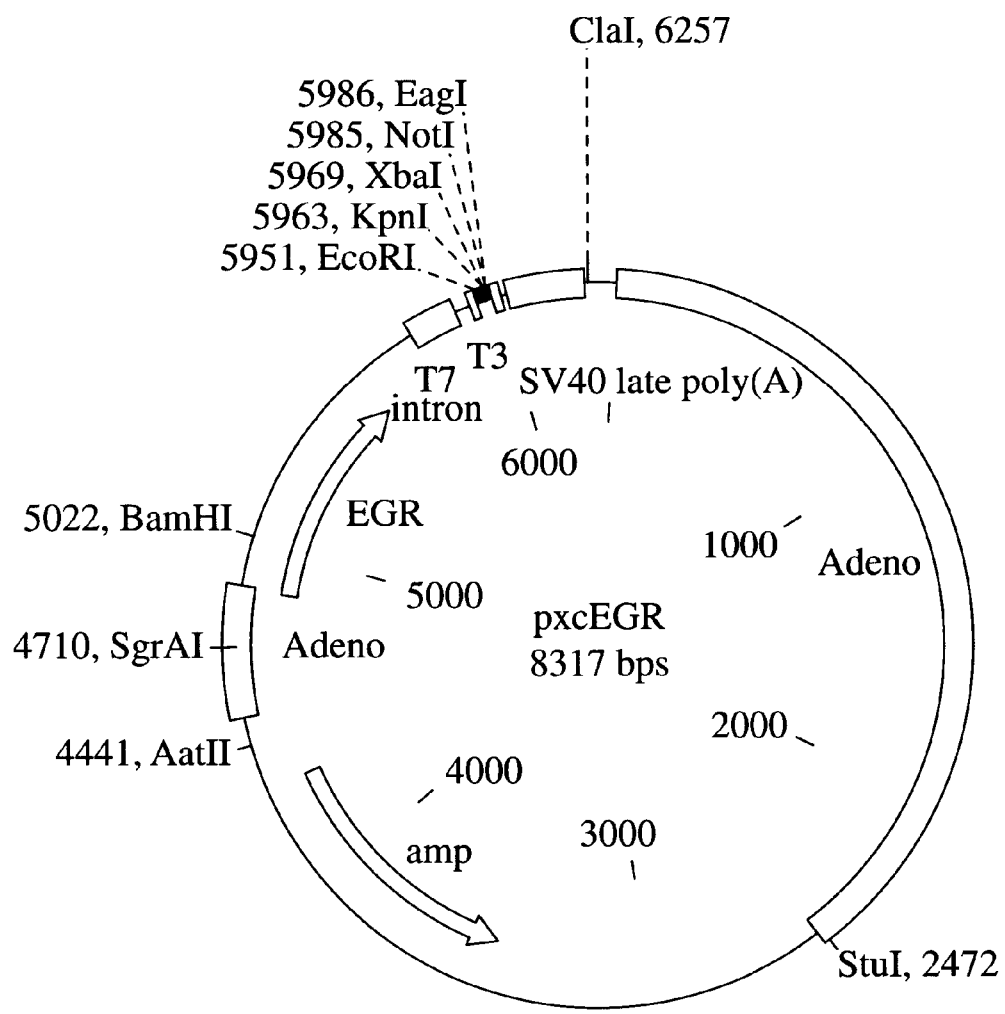
FIG. 4A is a restriction map of plasmid, pxcEGR, of Example 1.

The resulting 293 nt product is cleaved with Bgl II and Sac I and cloned into the Bgl II -Sac I sites of PSL 1180 (Pharmacia), and M13 forward and reverse primer are used to verify the sequence of the human MIP promoter. The Bgl II-Sac I fragment of the resulting plasmid, pSL 1180-MIP, is then excised and cloned into the Bgl II-Sac I sites of a CMV promoter deleted pCiNeo vector (Promega). This cloning is verified by digestion with Alw I. The resulting plasmid, pMIPiNeo, is then cleaved with Bgl II and Fsp I. The resulting 1435 nt fragment is then cloned into the Bam HI-Hpa I sites of pXC15–18 (FIG. 3). The resulting clone, pxcMIP, is verified by digestion with numerous restriction enzymes. A restriction map of this clone is given in FIG. 9A.

As described above for the pxcEGR clones of Example 1, four ORFs (encoding GFP, dominant negative RAS, non-phosphorylatable RB and Herpes Simplex type 1 thymidine kinase) are cloned into pxcMIP to form different recombinant 1 adenoviral vectors. The necessary enzymatic digestions for the pxcMIP clones and the sequencing of the junctions and ORF inserts of these clones are as described above for the pxcEGR clones.

Figure 10:
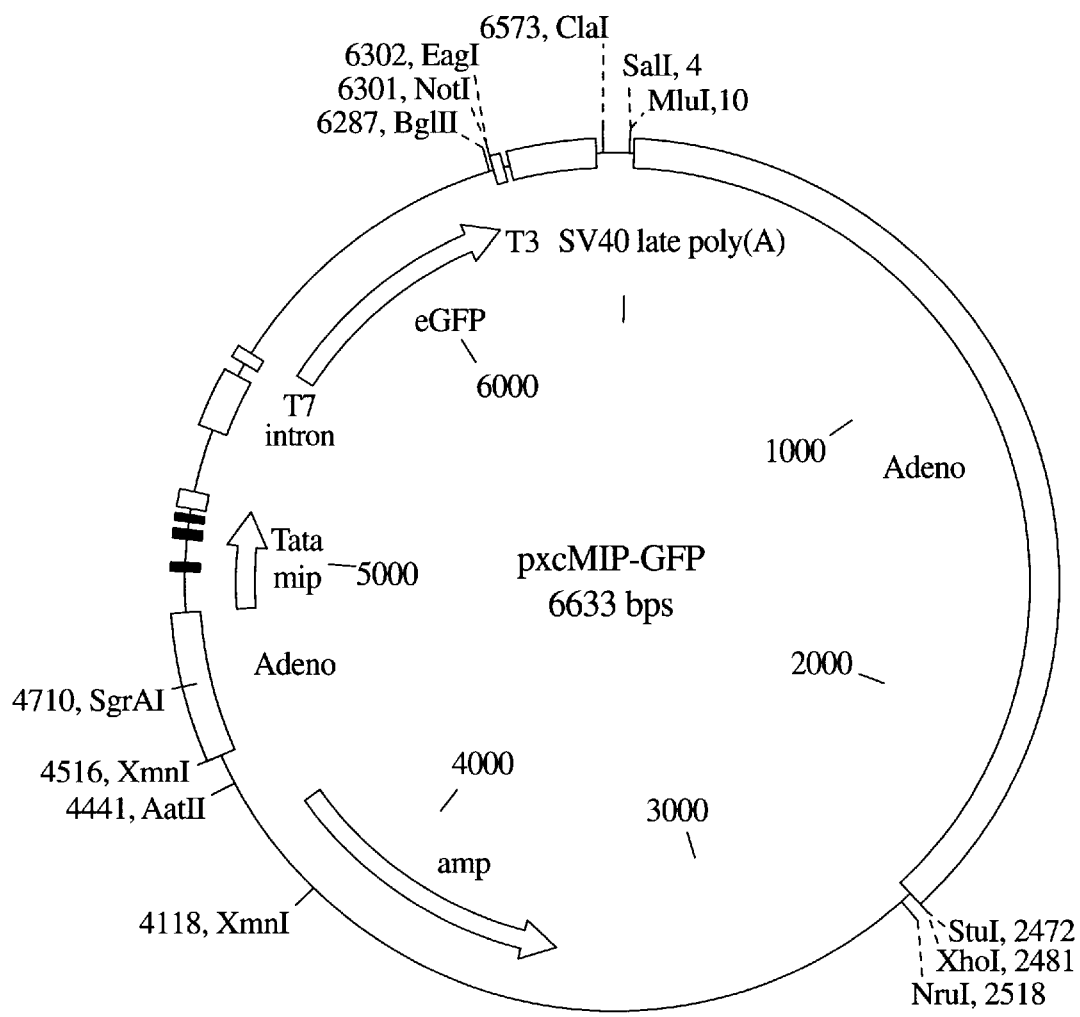
FIG. 10 is a restriction map of plasmid, pxcMIP-GFP, of Example 2.

GFP:

A 716 nt Nhe I-Sal I fragment containing the Enhanced Greeen Fluorescent Protein (GFP) is isolated from peGFP-C1 (Clontech) and cloned into the Nhe I-Sal I sites of pxcMIP. See restriction map of resulting plasmid, pxcMIP-GFP, in FIG. 10.

Figure 11:
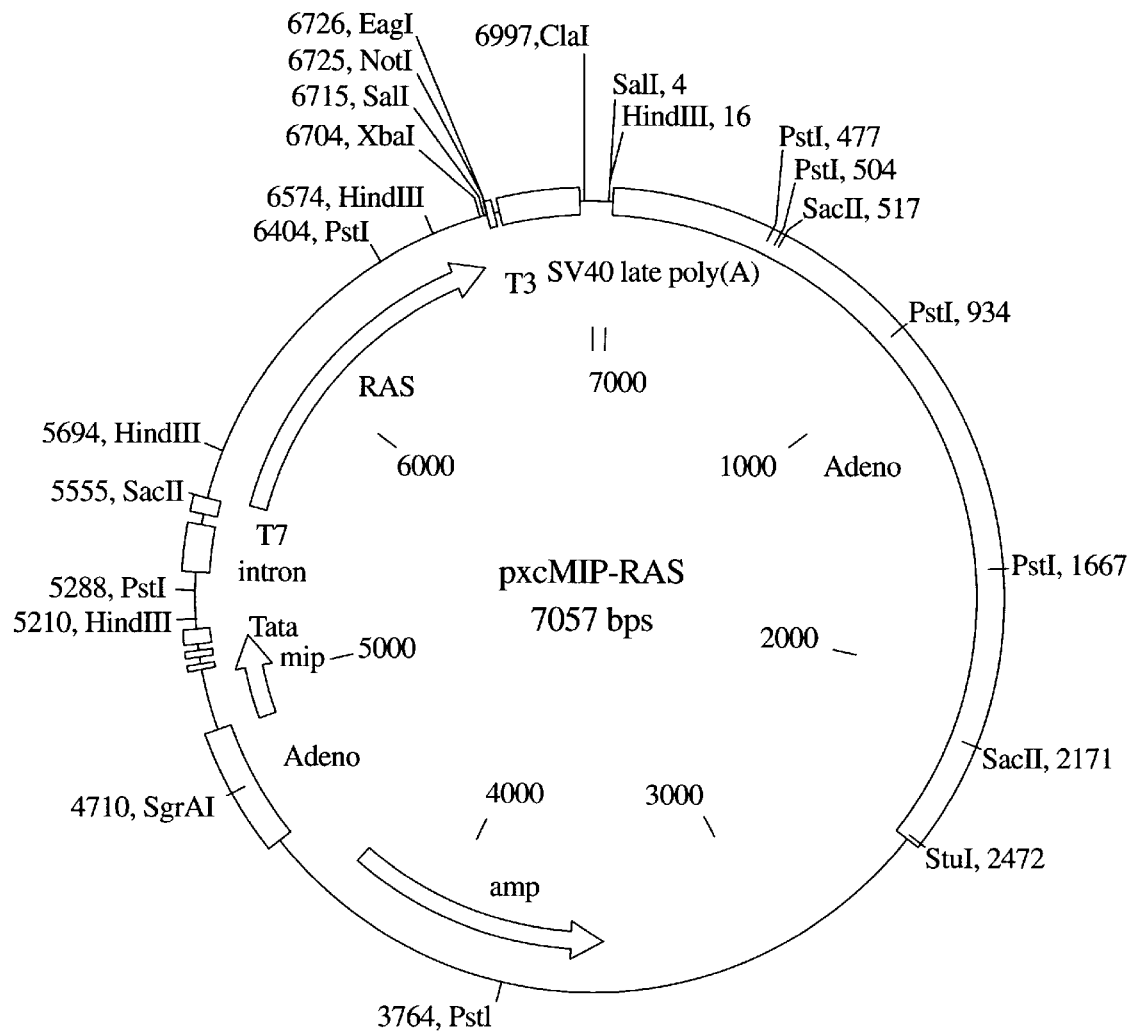
FIG. 11 is a restriction map of plasmid, pxcMIP-RAS, of Example 2.

Dominant negative RAS:

The Sac II (blunted)-Xba I fragment of dominant negative RAS cDNA is cloned into the Eco RI (blunted)-Xba I sites of pxcMIP. The correct clone is initially verified by restriction enzyme mapping. Sequencing of the junctions and the RAS cDNA insert are performed with T3 and T 7 primers (See Map). See restriction map of resulting plasmid, pxcMIP-RAS, in FIG. 11.

Figure 12:
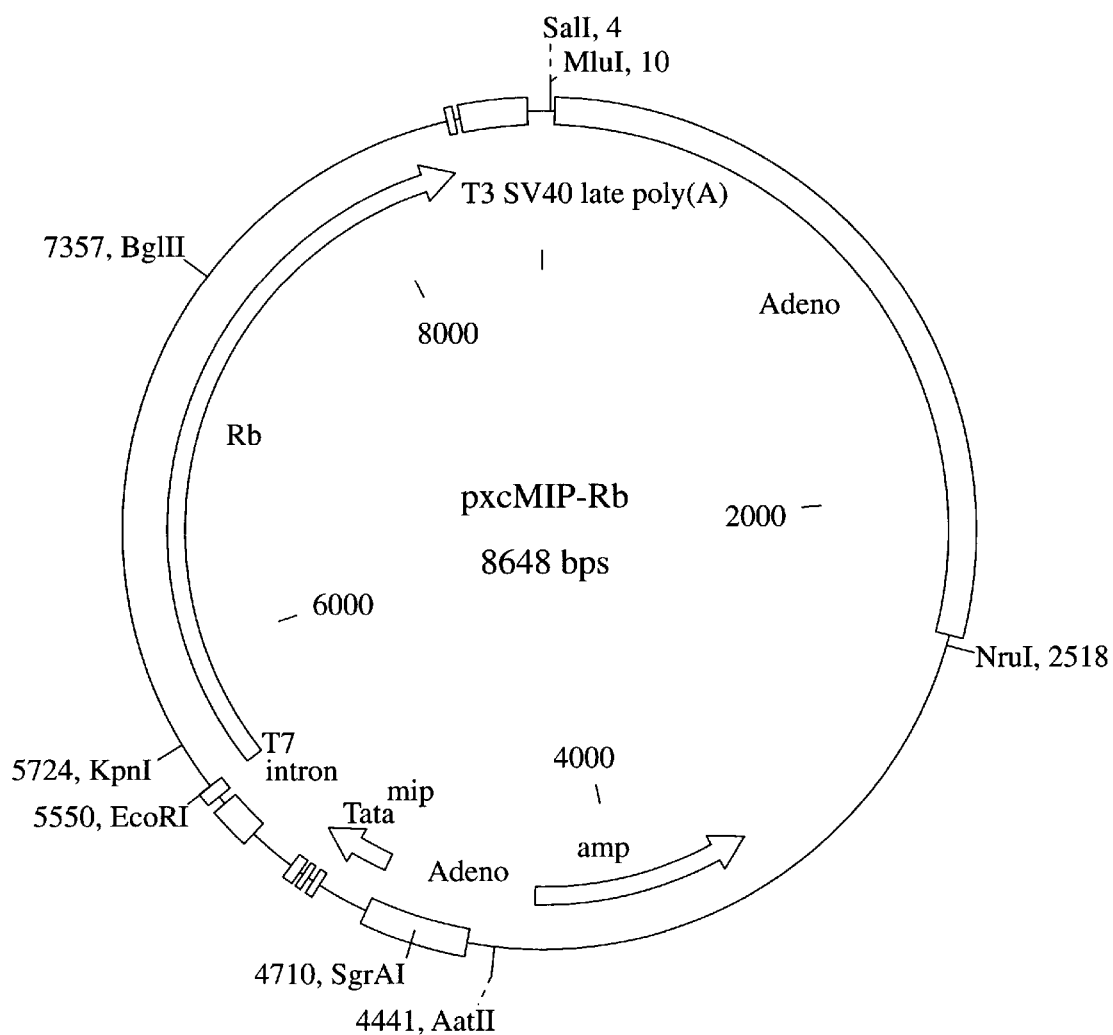
FIG. 12 is a restriction map of plasmid, pxcMIP-Rb, of Example 2.

Rb:

A 2768 nt Eco RI-Sau I (Klenow fill-in blunted) fragment from pECE34 is ligated into the Eco RI-Not I (Klenow fill-in blunted) sites of pxcMIP. The correct clone is initially identified by Sac I digestion. See restriction map of resulting plasmid, pxcMIP-Rb, in FIG. 12.

Figure 13:
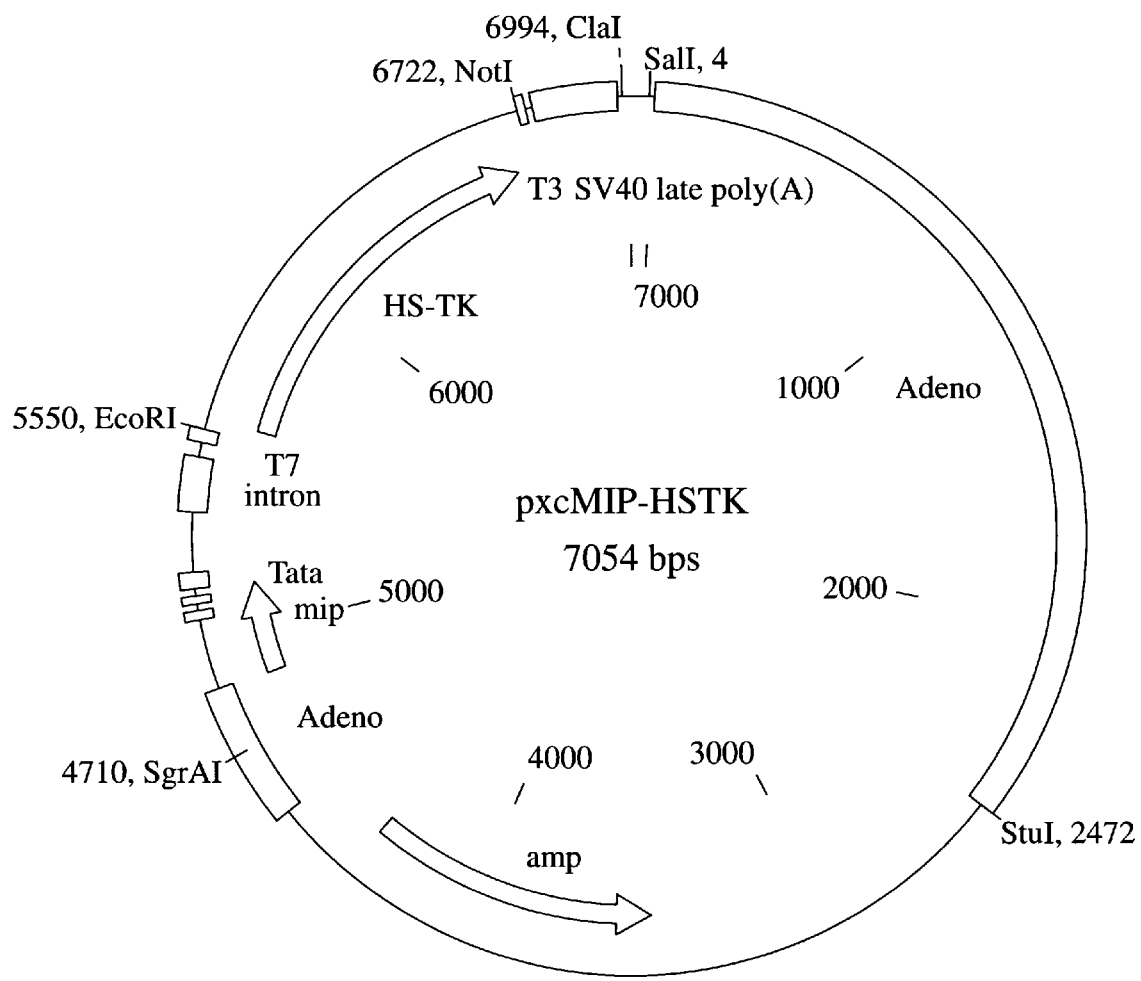
FIG. 13 is a restriction map of plasmid, pxcMIP-HSTK, of Example 2.

HSTK:

A 1176 nt fragment of the Herpes Simplex type 1 thymidine kinase ORF is cut with Hind III (rendered blunt by a Klenow fill-in reaction) and Eco RI. This fragment is then cloned into the Eco RI-Not I (blunted) site of pxcEGR. Sac I digestion is initially used to verify this clone. See restriction map of resulting plasmid, pxcMIP-HSTK, in FIG. 13.

EXAMPLE 3

Construction of an Adenovirus First Stage Vector (R'ecombinant 1) Containing a Composite 1 Promoter with Elements from Both the Rat EGR-1 (Early Growth Response) Gene and Major Intrinsic Protein (MIP) Gene Promoter Elements Plasmid pSL1180-MIP of Example 2 is cleaved with Bgl II, followed by a Klenow fill-in reaction. Both enzymes are heat inactivated, and then the plasmid is further digested with Sac I. The resulting 293 nts fragment is isolated from an agarose gel.

Plasmid pSL1180-EGR of Example I is digested with Sma I and Bgl II, and the resulting 282 nt fragment is isolated.

Figure 14:
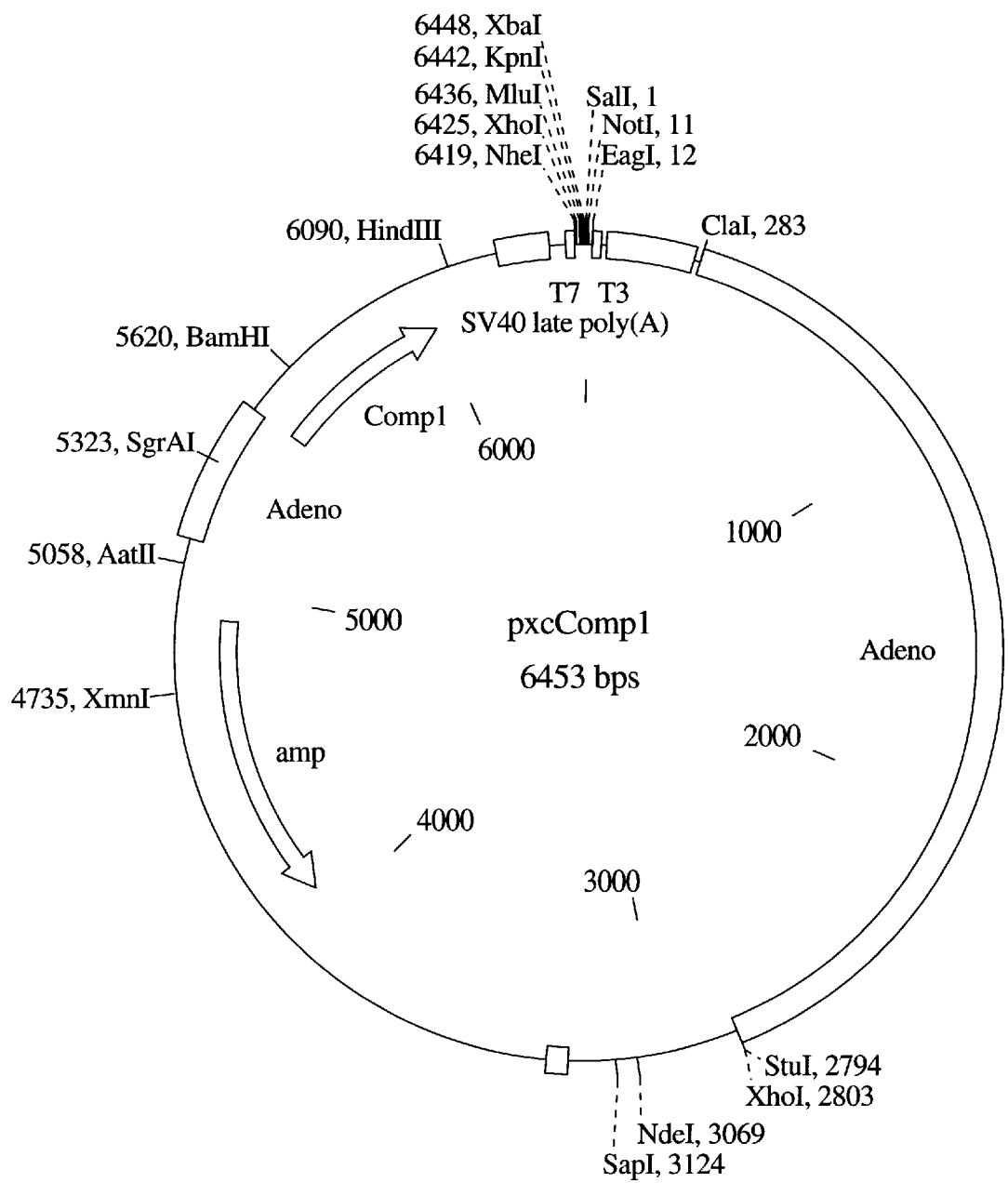
FIG. 14 is a restriction map of plasmid, pxcComp1, of Example 3.

The two DNA fragments are then ligated overnight at room temperature. A small aliquot (1/100 of a microliter) is then used as a template in a PCR, using the 5' EGR oligonucleotide of Example 1 and the 3' MIP oligonucleotide of Example 2. The resulting 585 nt composite promoter fragment is digested with Bgl II and Sac I and isolated from an agarose gel. This fragment is then ligated into the Bgl II Sac I sites of PSL 1180. Restriction enzyme digestion is used to initially confirm the cloned PCR product. After confirmation by sequencing of the composite promoter, the Bgl II-Sac I fragment is isolated and ligated into the Bgl II-Sac I sites of Bgl II-Sac I digested pCiNeo, thus replacing the CMV promoter with the composite promoter. This plasmid pCompiNeo is then digested with Bgl II and Fsp I. The resulting 1318 nt fragment is then ligated into the Bam HI-Hpa I sites of pXC15–18 (FIG. 3), resulting in the plasmid pxcComp1. A restriction map of pxcComp1 is given in FIG. 14, and the DNA sequence of its composite 1 promoter is shown in FIG. 14A.

As described above for the pxcEGR clones of Example 1, four ORFs (encoding GFP, dominant negative RAS, non-phosphorylatable RB and Herpes Simplex type 1 thymidine kinase) are cloned into pXComp1 to form different recombinant 1 adenoviral vectors. The necessary enzymatic digestions for the pXComp1 clones and the sequencing of the junctions and ORF inserts of these clones are as described above for the pxcEGR clones.

Figure 15:
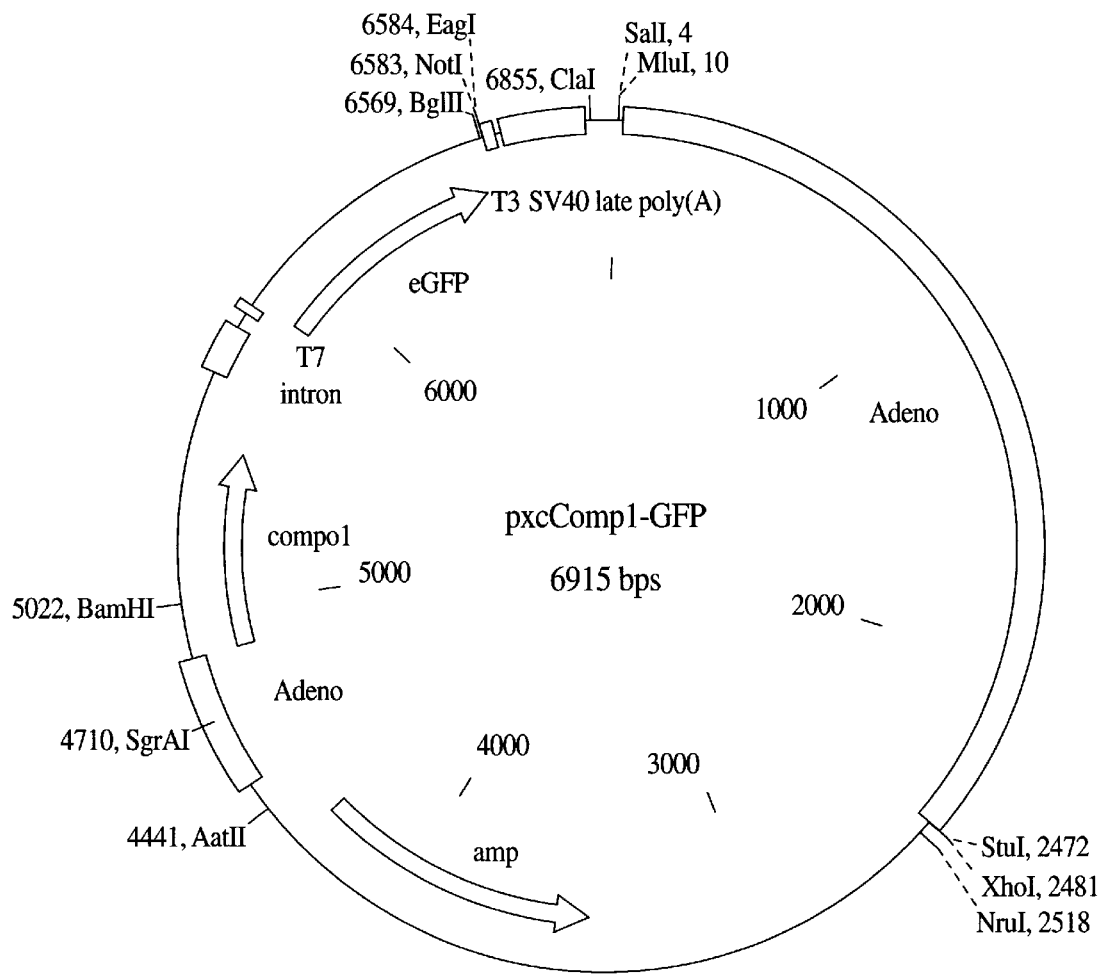
FIG. 15 is a restriction map of plasmid, pxcComp1-GFP, of Example 3.

GFP:

A 716 nt Nhe I-Sal I fragment containing the Enhanced Greeen Fluorescent Protein (GFP) is isolated from peGFP-C1 (Clontech) and cloned into the Nhe I-Sal I sites of pxComp1. See restriction map of resulting plasmid, pxcComp1-GFP, in FIG. 15.

Figure 16:
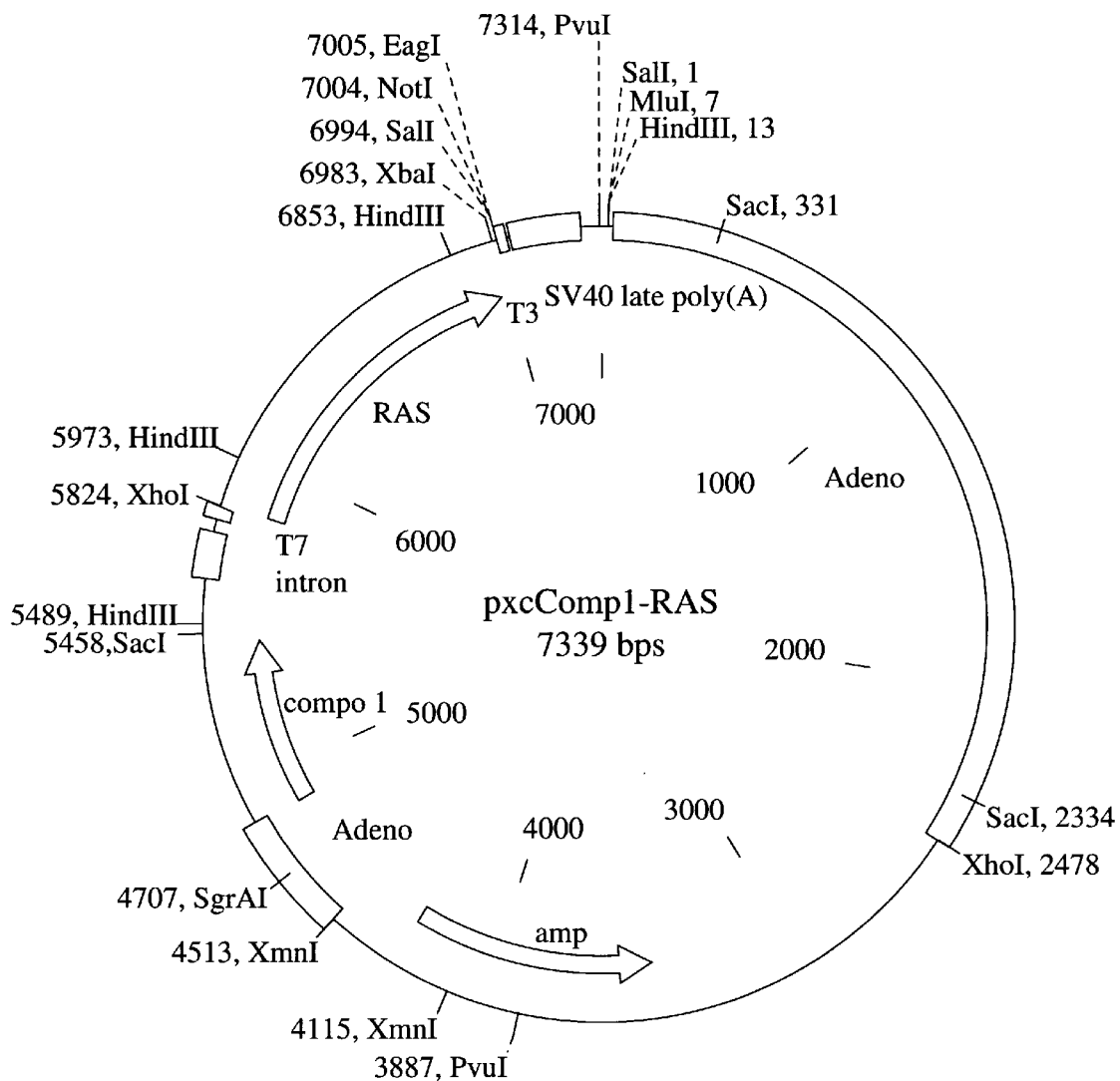
FIG. 16 is a restriction map of plasmid, pxcComp1-RAS, of Example 3.

Dominant negative RAS:

The Sac II (blunted)-Xba I fragment of dominant negative RAS cDNA of Example 1 is cloned into the Eco RI (blunted)-Xba I sites of pxcComp1. The correct clone is initially verified by restriction enzyme mapping. Sequencing of the junctions and the ras cDNA insert are performed with T3 and T 7 primers. See restriction map of resulting plasmid, pxcComp1-RAS, in FIG. 16.

Figure 17:
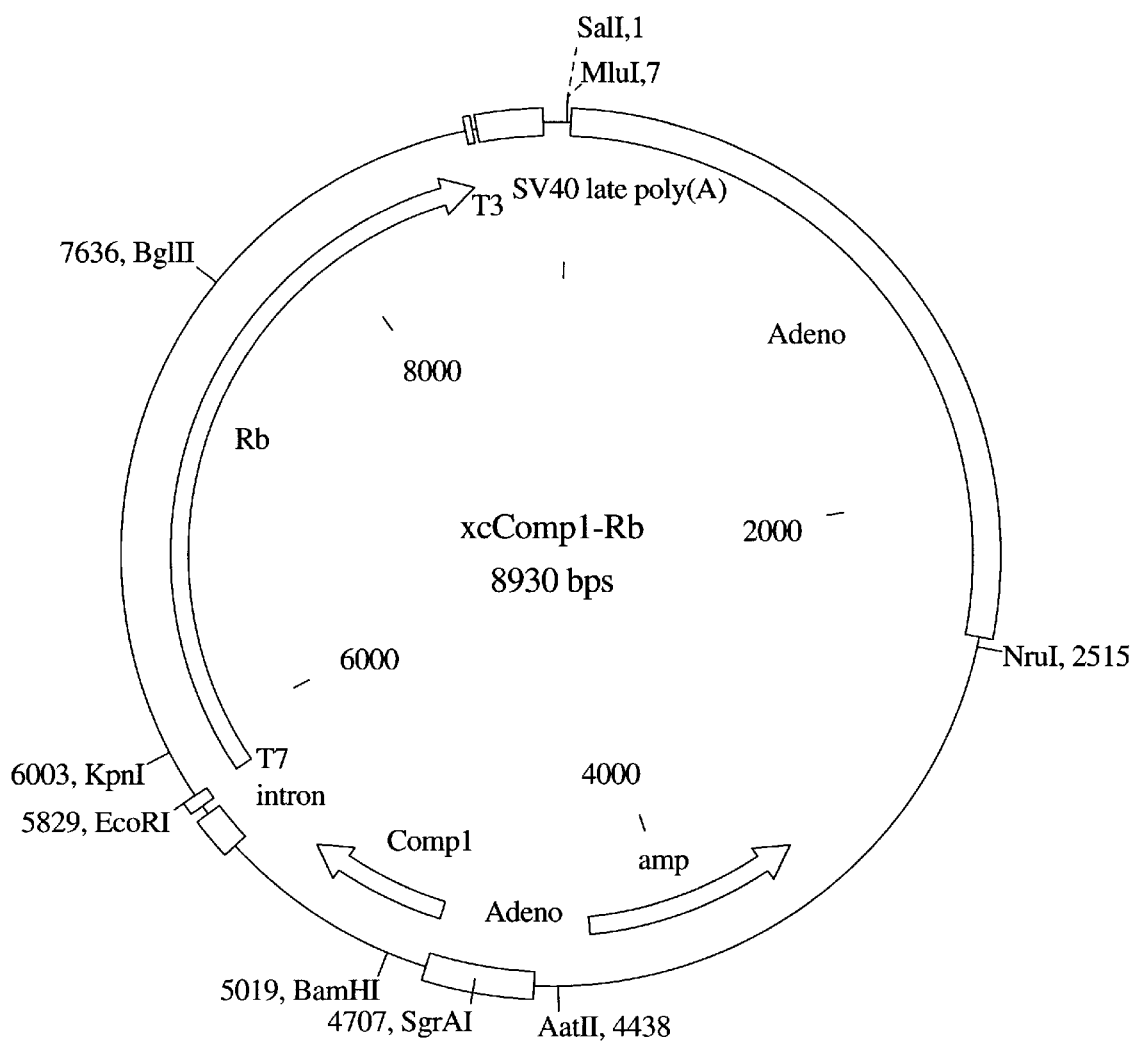
FIG. 17 is a restriction map of plasmid, pxcComp1-Rb, of Example 3.

Rb:

A 2768 nt Eco RI-Sau I (Klenow fill-in blunted) fragment from pECE34 is ligated into the Eco RI-Not I (Klenow fill-in blunted) sites of pxcomp1. The correct clone is initially identified by Sac I digestion. See restriction map of resulting plasmid, pxcComp1-Rb, in FIG. 17.

Figure 18:
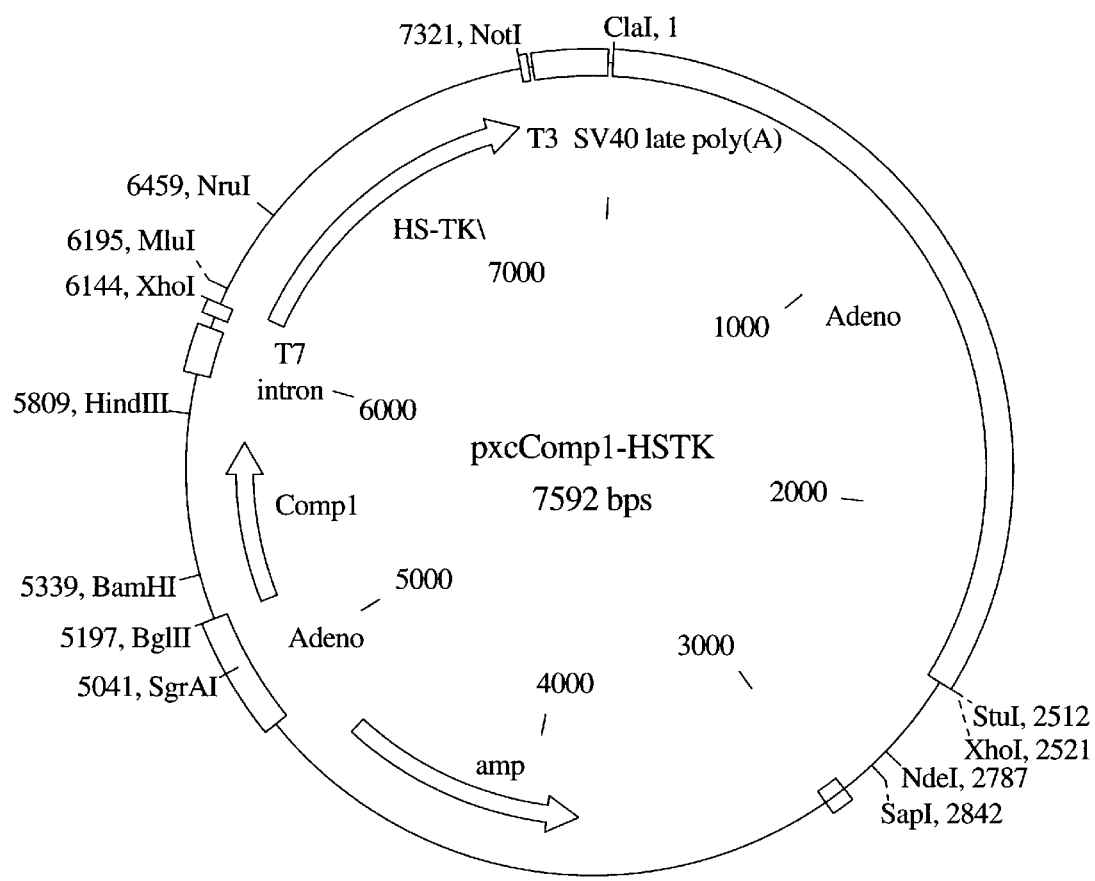
FIG. 18 is a restriction map of plasmid, pxcComp1-HSTK, of Example 3.

HSTK:

A 1176 nt fragment of the Herpes Simplex type 1 thymidine kinase ORF is cut with Hind III (rendered blunt by a Klenow fill-in reaction) and Eco RI. This fragment is then cloned into the Eco RI-Not I (blunted) site of pxcComp1. Sac I digestion is initially used to verify this clone. See restriction map of resulting plasmid, pxcComp1-HSTK, in FIG. 18.

Figure 19A:
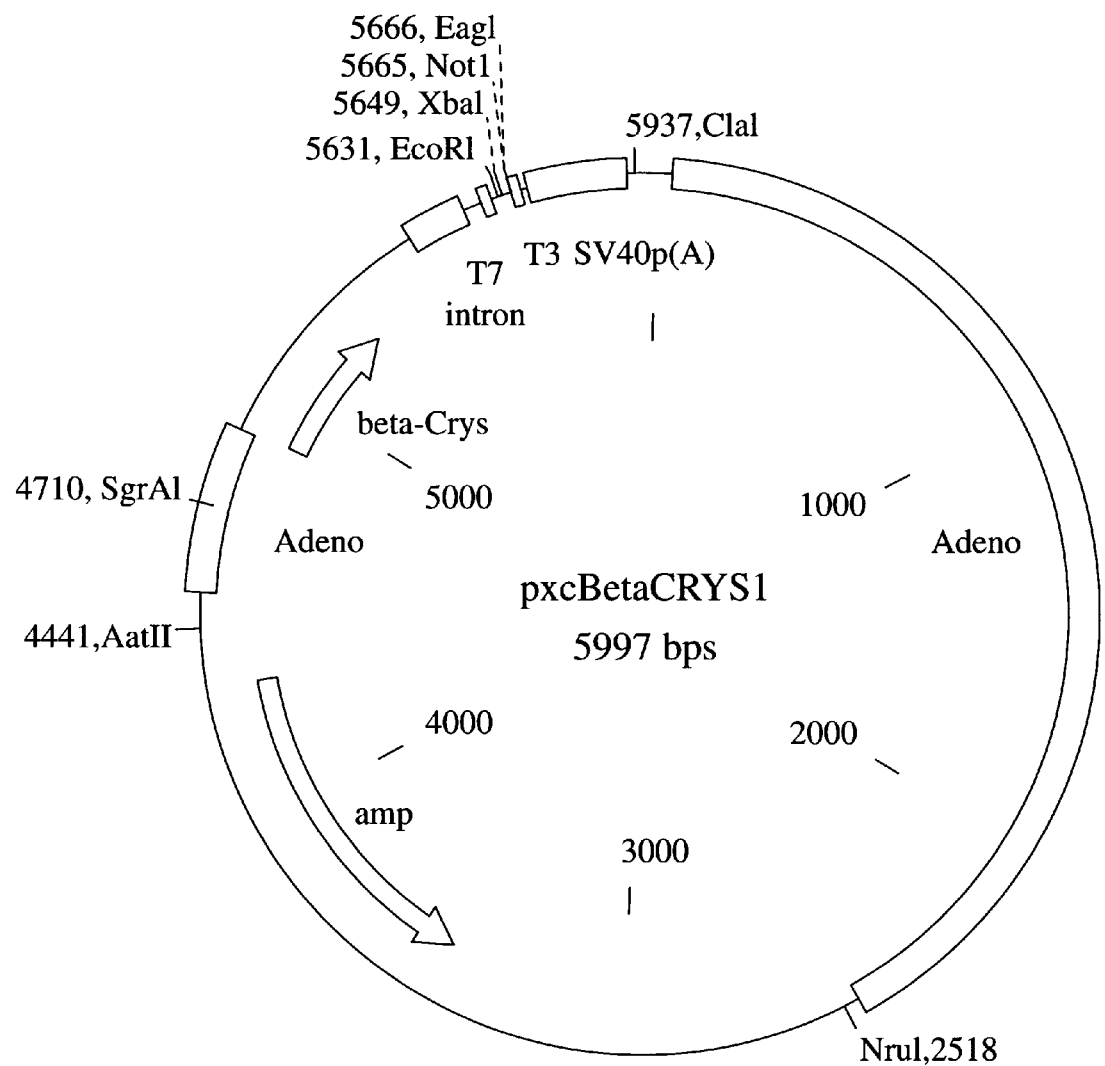
FIG. 19A is a restriction map of the plasmid, pxcCrys1, of Example 4.

EXAMPLE 4
Construction of an Adenovirus First Stage Vector (Recombinant 1) Containing the Human β-crystallin A3/A1 Gene Promoter Amplification of the human β-crystallin A 3/A1 gene promoter (shown in FIG. 19) is accomplished by PCR. A 5' oligonucleotide corresponding to −330 nt to −311 nt of the transcription start site containing a synthetic Bgl II site at its 5' end is used in conjunction with a 3' oligonucleotide complementary to +26 nt to +45 nt with a synthetic Sac I site.

```
5' primer   Bgl II              (SEQ ID NO:12)
GAAGA   TCTCCCAGGGTCTTAAGGT

3' primer   Sac I               (SEQ ID NO:13)
GAAGAGCTCT   TACTCACCCAGCTCCTGC
5' primer   Bgl II              (SEQ ID NO:12)
GAAGA   TCTCCCAGGGTCTTAAGGT
3' primer   Sac I               (SEQ ID NO:13)
GAAGAGCTCT   TACTCACCCAGCTCCTGC
```

The resulting 375 nt product is cleaved with Bgl II and Sac I and cloned into the Bgl II-Sac I sites of PSL 1180 (Pharmacia), and M13 forward and reverse primer are used to verify the sequence of the human -crystallin A 3/A1 gene promoter. The Bgl II-Sac I fragment of the resulting plasmid, pSL 1180-Crys is then excised and cloned into the Bgl II-Sac I sites of a CMV promoter deleted pCiNeo vector (Promega). This cloning is verified by restriction enzyme digestion. The resulting plasmid, pcrystiNeo, is then cleaved with Bgl II and Fsp I. The resulting 1335 nt fragment is then cloned into the Bam HI-Hpa I sites of pXC15–18 (FIG. 3). The resulting clone, pxcCrys1, is verified by digestion with numerous restriction enzymes. A restriction map of this clone is given in FIG. 19A.

As described above for the pxcEGR clones of Example 1, four ORFs (encoding GFP, dominant negative RAS, non-phosphorylatable RB and Herpes Simplex type 1 thymidine kinase) are cloned into pxcCrys1 to form different recombinant 1 adenoviral vectors. The necessary enzymatic digestions for the pxcCrys clones and the sequencing of the junctions and ORF inserts of these clones are as described above for the pxcEGR clones.

EXAMPLE 5
Construction of an Adenovirus First Stage Vector (Recombinant 1) Containing a Composite 2 Promoter with Elements from Both the Rat EGR-1 (Early Growth Response) gene and human β-crystallin Gene Promoter Elements Plasmid pSL1180-Crys of Example 4 is cleaved with Sca I and Sac I. The resulting 305 nt fragment is isolated from an agarose gel.

Plasmid pSL1180-EGR of Example 1 is digested with Sma I and Bgl II, and the resulting 282 nt is isolated.

Figure 20:
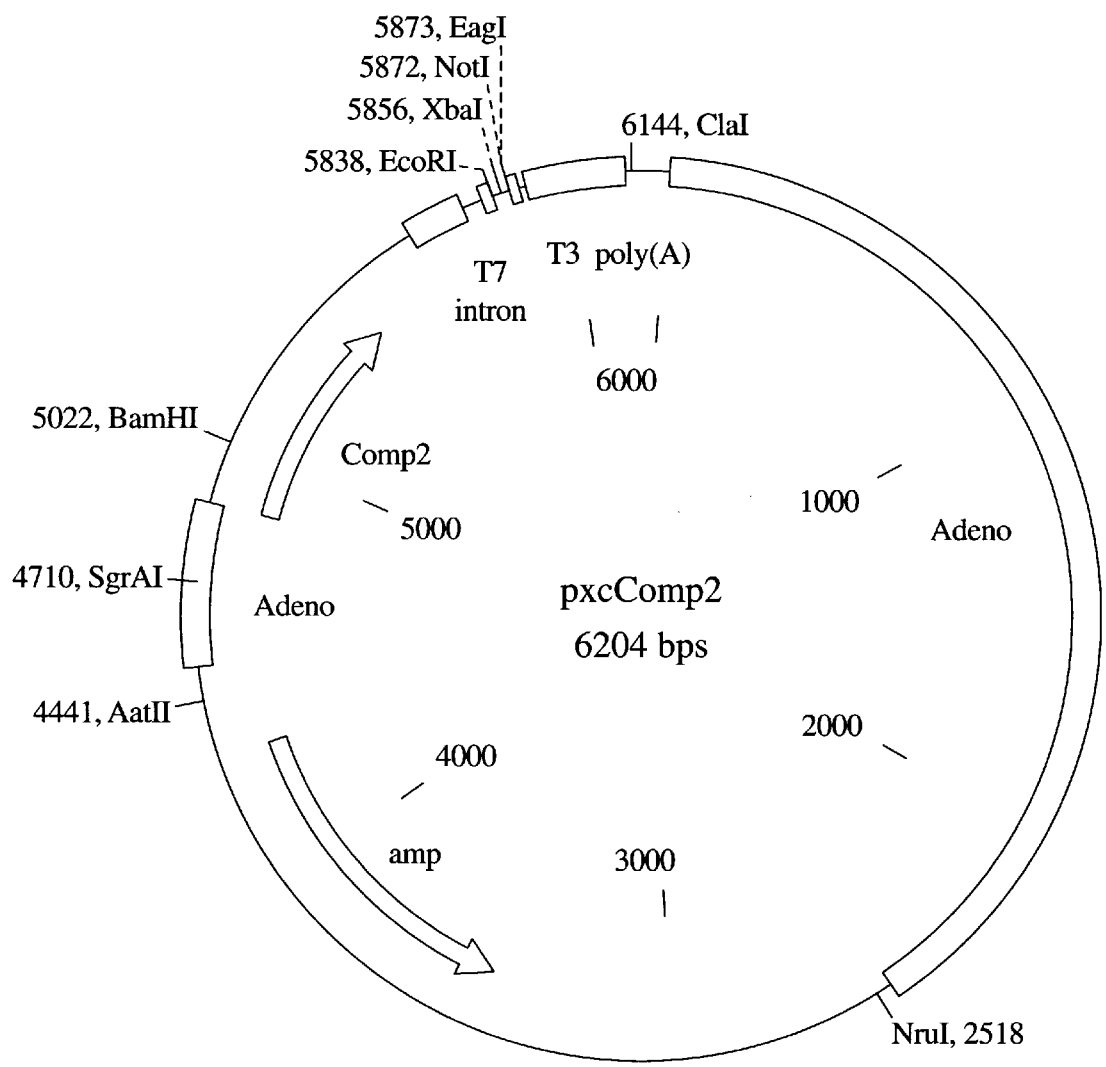
FIG. 20 is a restriction map of plasmid, pxcComp2, of Example 5.

The two DNA fragments are then ligated overnight at room temperature. A small aliquot (1/100 of a microliter) is then used as a template in a PCR, using the 5' EGR oligonucleotide of Example 1 and the 3' -crys oligonucleotide of Example 4. The resulting 587 nt composite promoter fragment is digested with Bgl II and Sac I, isolated from an agarose gel and ligated into the Bgl II Sac I sites of PSL 1180. Restriction enzyme digestion is used to confirm initially the cloned PCR product. After confirmation by sequencing of the composite promoter, the Bgl II-Sac I fragment is isolated and ligated into the Bgl II-Sac I sites of Bgl II, Sac I digested pCiNeo, thus replacing the CMV promoter with the composite promoter. This plasmid pComp2iNeo is then digested with Bgl II and Fsp I. The resulting 1318 nt fragment is then ligated into the Bam HI-Hpa I sites of pXC15–18 (FIG. 3), resulting in the plasmid pxcComp2. A restriction map of pxcComp2 is given in FIG. 20, and the DNA sequence of its composite 2 promoter is shown in FIG. 20A.

As described above for the pxcEGR clones of Example 1, four ORFs (encoding GFP, dominant negative RAS, non-phosphorylatable RB and Herpes Simplex type 1 thymidine kinase) are cloned into pxcComp2 to form different recombinant 1 adenoviral vectors. The necessary enzymatic digestions for the pxCOMP2 clones and the sequencing of the junctions and ORF inserts of these clones are as described above for the pxcEGR clones.

EXAMPLE 6
Evaluation of Promoter Constructs of Examples 1–5

The proper functioning of the EGR-1 elements in the simple EGR-1 promoter construct, as well as in the composite promoter constructs, is tested by serum deprivation-refeeding of transiently transfected cell lines. Refeeding of serum rapidly induces expression of ORFs downstream of this promoter.

The correct functioning of MIP elements in both the simple MIP promoter construct and in its composite promoter constructs is tested by expression following infection of in vitro cultures of lens capsular sacs of pig eyes which have undergone cataract surgery (Liu, C. et al., 1996; Wormstone et al., 1997).

Likewise, the correct functioning of β-crystallin elements in both the simple β-crystallin promoter construct and in its composite promoter constructs is tested by expression following infection of in vitro cultures of lens capsular sacs of pig eyes which have undergone cataract surgery.

Confirmation of the proper functioning of each portion of the composite promoters is achieved by analysis of GFP expression following: 1. Transient transfection of EB cells (human colon cell line) for the EGR elements and 2. recombinant adenovirus infection of in vitro cultures of lens capsular sacs of pig eyes which have undergone cataract surgery. An intact MIP promoter construct and an intact β-crystallin promoter construct serve as controls. As a test of GFP detection and expression, a CMV promoter construct is also tested in parallel to assess transfection efficiency in the two cell types.

EXAMPLE 7
Creation of a Sub-line of the 293 Cell Line with Metal Inducible Expression of the Adenovirus E4 ORF 6

Figure 21:
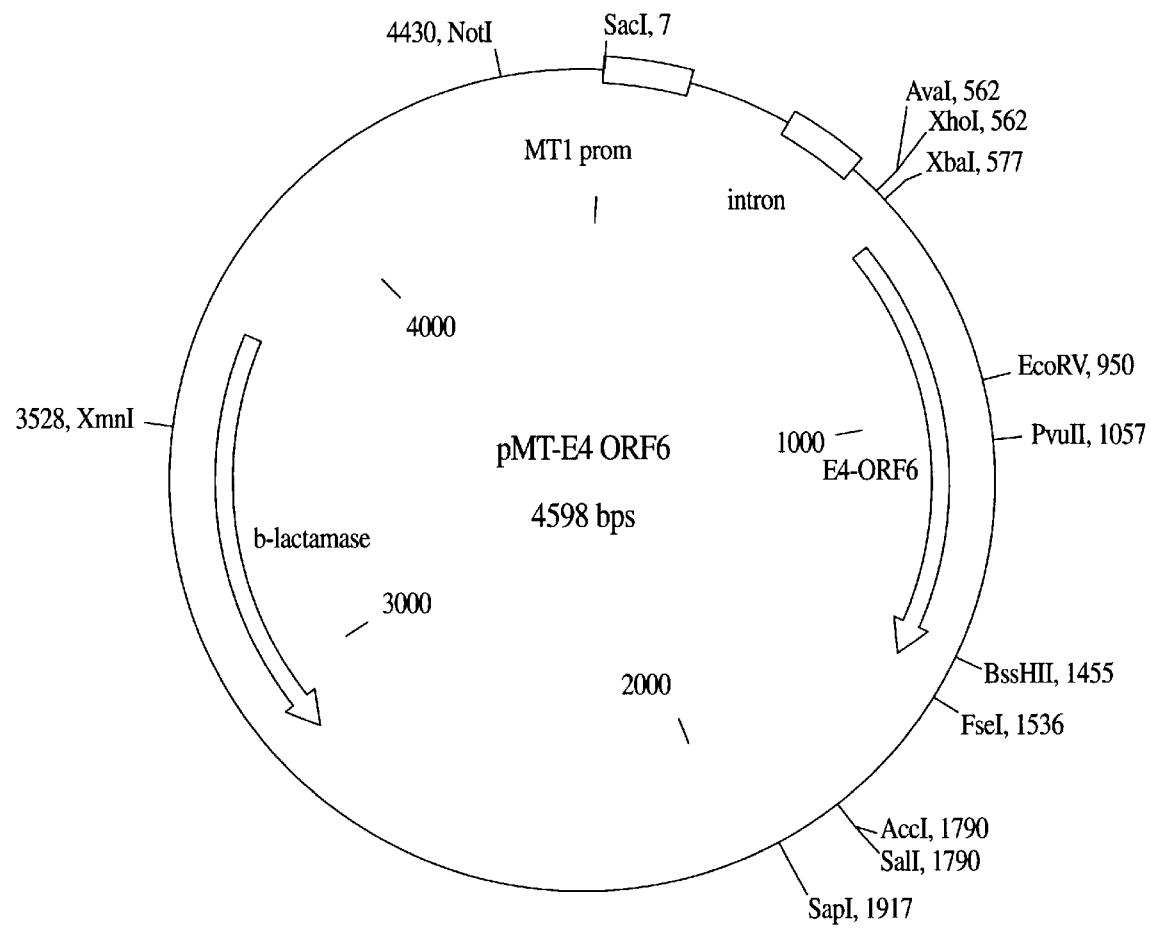
FIG. 21 is a restriction map of the plasmid, pMT-E4 ORF6, of Example 7.

The 884 nt Bam HI fragment of CMV-ORF 6 obtained from Goran Akusjarvi (Uppsala, Sweden) is cloned into the Bam HI site of a metallothionein promoter vector pMT, giving rise to the clone pMT-E4 ORF6 (Shaw et al., 1992) (FIG. 21). Correct orientation of the ORF 6 is evaluated with the restriction enzyme Kpn I. The MT-E4 ORF6 is then co-transfected with the PCI-neo plasmid (Promega) into the 293 cell line (Graham et al., 1977). After three weeks of selection, G418-resistant clones are isolated and characterized for inducible ORF6 expression by Northern analysis.

EXAMPLE 8
Recombinant Adenovirus Production, Purification and Characterization To produce different replication-defective recombinant adenoviruses of this invention, 293/MT-E4 ORF6 cells are plated at 70–80% confluence, then co-transfected with each one of the pxc (recombinant 1) adenoviral vectors of Examples 1–5 and a modified pJM17 plasmid lacking E4 ORF 6 (Bett et al., 1994), using calcium phosphate (Chen and Okayama, 1987). After 10 days, the cells are frozen and thawed three times in 1 ml of culture media and centrifuged to remove cellular debris. This freeze-thaw extract is then titered according to standard procedures on 293 cells overlaid with soft agar. Individual plaques (3 per desired recombinant adenovirus) are picked and eluted in 1 ml of culture media. The individual plaques are then again titered on 293/MT-E4 ORF6 cells, and the virus purification is repeated a total of three times.

Recombinant adenovirus stocks are then twice purified on $CsCl_2$ gradients to remove contaminating cellular proteins. The individual titers of recombinant adenovirus preparations are determined on 293 cells as described for the isolation of individual plaques, namely on soft agar-overlaid cultures of infected 293 cells. DNA isolated from each virus is analysed by diagnostic restriction enzyme mapping.

References

Bett, A J., Prevec, L. and Graham, F L. (1993) Packaging capacity and stability of human adenovirus type 5 vectors. J Virol 67: 5911–21.

Bett, A J., Haddara, W., Prevec, L., and Graham, F L. (1994) An efficient and flexible system for construction of adenovirus vectors with insertions or deletions in early regions 1 and 3. Proc. Natl Acad. Sci. U S A. 91 (19):8802–6.

Blomstedt, G., Fagerholm, P., Gallo, J., and Philipson, B. (1987) After-cataract in the rabbit eye following extracapsular cataract extraction—a wound healing reaction. Acta Opthalmologica 67, 93–99.

Chang, M., Barr, E., Seltzer, J., Jiang, Y., Nabel, G., Nabel, E., Parmacek, M. and Leiden, J. (1995) Cytostatic Gene Therapy for Vascular Proliferative Disorders with a Constituitively Active Form of the Retinoblastoma Gene Product. Science 267, 518–522.

Chen, C. and Okayama, H. (1987) High-Efficiency Transformation of Mammalian Cells by Plasmid DNA. Molec. And Cellular Biol. 7 (8), 2745–52.

Chepelinsky, A B., Piatigorsky, J., Pisano, M M., Dubin, R A., Wistow, G., and Limjoco, T I., Klement, J F., and Jaworski, C J. (1991) Lens protein gene expression: alpha-crystallins and MIP. Lens & Eye Toxicity Research. 8(2–3):319–44.

Clive, D., Turner, N T.. Hozier, J., Batson, A G. and Tucker, W E. Jr. (1983) Preclinical toxicology studies with acyclovir: genetic toxicity tests. Fundamental & Applied Toxicology. 3(6):587–602, 1983 November–December.

Dobner, T., Horikoshi, N., Rubenwolf, S., and Shenk, T. (1996) Blockage by Adenovirus E4orf6 of Transcriptional Activation by the p53 Tumor Suppressor. Science 272 1470–1473.

Graham, F. L., Smiley, J., Russell, W. C. and Nairn, R. (1977) Characteristics of a human cell line transformed by DNA from Human Adenovirus type 5. J. General Virology 36 (1) 59–74.

Hamel, P., Gill, R., Phillips, R., and Gallie, B. (1992) Regions controlling hyperphosphorylation and conformation of the retinoblastoma gene product are independent of domains required for transcriptional repression. Oncogene 7(4):693–701.

Hangai, M., Kaneda, Y., Tanihara, H., and Honda, Y. (1996) In vivo gene transfer into the retina mediated by a novel liposome system. Investigative Ophthalmology & Viral Science 37(13): 2678–2685.

Hitt, M., Bett, A., Prevec, L., and Graham, F. (1994) Construction and Propagation of Human Adenovirus Vectors. Cell Biology: A Laboratory Handbook, Academic Press Inc. 479–490.

Indolfi, C., Avvedimento, E., Rapacciuolo, A., Di Lorenzo, E., Esposito, G., Stabile, E., Feliciello, A., Mele, E., Giuliano, P., Condorelli, G., and Chiariello, M. (1995) Inhibition of cellular ras prevents smooth muscle cell proliferation after vascular injury in vivo. Nature Medicine 1, 541–545.

Kamb, A., Gruis, N., Weaver-Feldhaus, J., Liu, Q., Harshman, K., Tavtigian, S V., Stockert, E., Day, R., Johnson, B., and Skolnick M H. (1994) A cell cycle regulator potentially involved in genesis of many tumor types. Science 264(5157):436–40.

Kaplan, J B. (1994) Biological activity of human N-ras and K-ras genes containing the Asn17 dominant negative mutation. Oncology Research 6, 611–5.

Kearns, W G., Afione, S A., Fulmer, S B., Pang, M C., Erikson, D., Egan, M., Landrum, M J., Flotte, T R., and Cutting, G R. (1996) Recombinant adeno-associated virus (AAV-CFTR) vectors do not integrate in a site-specific fashion in an immortalized epithelial cell line. Gene Therapy 3(9):748–55.

Kiesling, M. and Gass, P. (1993) Immediate early gene expression in experimental epilepsy. Brain Pathology 3, 381–393.

Kondoh, H., Katoh, K., Takahashi, Y., Goto, K., Hayashi, S., and Okada, T S. (1988) Developmental regulation of the chicken delta 1-crystallin gene: analysis by transgenesis and gene dissection. Cell Differentiation & Development. 25 Suppl:53–57.

Kozarsky, K. F. and Wilson, J. M. (1993) Gene therapy: adenovirus vectors Current Opinion in genetics and development, 3:499–503.

Liu, C., Wormstone, I., Duncan, G., Marcantonio, J., Webb, S., and Davie, P. (1996) A study of human lens cell growth in vitro: A model for posterior capsule opacification. Invest. Opthalmology and Visual Science 37 (5) 906–914.

Liu, M L., Winther, B L., and Kay, M A. (1996) Pseudotransduction of hepatocytes by using concentrated pseudotyped vesicular stomatitis virus G glycoprotein (VSV-G)-Moloney murine leukemia virus-derived retrovirus vectors: comparison of VSV-G and amphotropic vectors for hepatic gene transfer. Journal of Virology 70(4):2497–502.

Marshall, J., Molloy, R., Moss, G W., Howe, J R., and Hughes, T E. (1995) The jellyfish green fluorescent protein: a new tool for studying ion channel expression and function. Neuron. 14 (2):211–5.

Mittal, S K., Bett, A J., Prevec, L. and Graham, F L. (1995) Foreign gene expression by human adenovirus type 5-based vectors studied using firefly luciferase and bacterial beta-galactosidase genes as reporters. Virology 210: 226–230.

Nischi, O. (1986) Incidence of posterior capsule opacification in eyes with and without posterior chamber intraocular lenses. J. Cataract Refract. Surg. 12, 519–522.

Ogiso, Y., Sakai, N., Watari, H., Yokoyama, T., and Kuzumaki N. (1994) Suppression of various human tumor cell lines by a dominant negative H-ras mutant. Gene Therapy. 1(6):403–7.

Peek, R. Niessen, R. Schoenmakers, J., and Lubsen, N. (1991) DNA methylation as a regulatory mechanism in rat -crystallin gene expression. Nucleic Acids Research 19(1), 77–83.

Piatigorsky, J. (1989) Lens crystallins and their genes: diversity and tissue-specific expression. FASEB Journal. 3(8): 1933–40.

Russ, A P., Friedel, C., Grez, M., and von Melchner, H. (1996) Self-deleting retrovirus vectors for gene therapy. Journal of Virology 70(8):4927–32.

Salvensen, S., Eide, N., and Syrdalen, P. (1991) Retinal detachment after YAG-laser capsulotomy. Acta Ophtalmologica 69, 61–64.

Shaw, P., Freeman, J., Bovey, R., and Iggo, R. (1996) Regulation of specific DNA binding by p53: evidence for a role for O-glycosylation and charged residues at the carboxy-terminus. Oncogene, 12: 921–930

Shaw, P., Tardy, S., Bovey, R., Sahli, R., Sordat, B., and Costa, J. (1992) Inducion of apoptosis by wt p53 in a colon tumor-derived cell line. Proc. Nat. Acad. Sci. U.S.A.

Simons, M., Edelman, E., DeKyser, J-I., Langer, R., and Rosenberg, R: (1992) Antisense c-myb oligonucleotides inhibit intimal arterial smooth muscle cell accumulation in vivo. Nature 359, 67–70.

Sung, Y J., Hwang, M C., and Hwang, Y W. (1996) The dominant negative effects of H-Ras harboring a Gly to Ala mutation at position 60. Journal of Biological Chemistry 271 (48):30537–43.

Waldman, A S., Haeusslein, E., and Milman, G. (1983) Purification and characterization of herpes simplex virus (type 1) thymidine kinase produced in *Escherichia coli* by a high efficiency expression plasmid utilizing a lambda PL promoter and cl857 temperature-sensitive repressor. Journal of Biological Chemistry 258(19):11571–5.

Weichselbaum, R., Hallahan, D., Fuks, Z. and Kyfe, D. (1994) Radiation induction of immediate early genes: effectors of the radiation-stress response. International Journal of Radiation Oncology, Biology, Physics 30, 229–234.

Wills, Maneval, D., Menzel, P., Harris, M., Sutjipto, s., Vaillancourt, M. Huang, W., Johson, D., Anderson, S., Wen, S., Bookstein, R., Shepard, H., and Gregory, R. (1994) Development and Characterization of Recombinant Adenoviruses Encoding Human p53 for Gene Therapy of Cancer. Human Gene Therapy 5:1079–108.

Wormstone, I., Liu, C., Rakic, J., Marcantonio, J,., Vrensen, G., and Duncan, G. (1997) Human lens epithelial cell proliferation in a protein-free medium Investigative. Ophthalmology & Visual Science 38(2):396–404.

Wu, H., Wade, M., Krall, L., Grisham, J., Xiong Y. and Van Dyke, T. (1996) Targeted in vivo expression of the cyclin-dependent kinase inhibitor p21 halts hepatocyte cell-cycle progression, postnatal liver development and regeneration. Genes & Development. 10(3):245–60.

Xiao, X., Li, J., and Samulski, R J. (1996) Efficient long-term gene transfer into muscle tissue of immunocompetent mice by adeno-associated virus vector. Journal of Virology 70(11), 8098–108.

What is claimed is:

1. A replication-defective recombinant virus, said virus comprising:
   (a) an open reading frame (ORF) selected from the group consisting of:
      i) a dominant negative codon 116 mutant of a human RAS ORF;
      ii) a herpes simplex type I thymidine kinase ORF; and
      iii) a non-phosphorylatable retinoblastoma ORF; and
   (b) a promoter sequence selected from the group consisting of:
      i) a promoter comprising the human Major Intrinsic Protein gene promoter from −259 nt to +34 nt (SEQ ID NO:2); and
      ii) a promoter comprising the human βA3/A1-crystallin gene promoter from −345 nt to +45 nt (SEQ ID NO:4);

wherein said ORF is under the control of said promoter sequence.

2. The replication-defective recombinant virus of claim 1 which is an adenovirus.

3. The replication-defective recombinant virus of claim 2, wherein said virus lacks E1a, E1b, and E4 ORF 6.

4. The replication-defective recombinant virus of claim 1, wherein the promoter sequence is non-methylated.

5. The replication-defective recombinant virus of claim 1, wherein the promoter sequence is a composite promoter sequence further comprising a rat Early Growth Response-1 gene promoter sequence, wherein the composite promoter sequence comprises a sequence selected from the group consisting of SEQ ID NO:3 and SEQ ID NO:5.

* * * * *